US010058242B2

(12) United States Patent
Gomi et al.

(10) Patent No.: US 10,058,242 B2
(45) Date of Patent: Aug. 28, 2018

(54) OPHTHALMOLOGIC IMAGING APPARATUS AND OPHTHALMOLOGIC IMAGE DISPLAY APPARATUS

(71) Applicant: KABUSHIKI KAISHA TOPCON, Tokyo (JP)

(72) Inventors: Fumi Gomi, Osaka (JP); Masahiro Akiba, Toda (JP); Tsutomu Kikawa, Tokyo (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 0 days.

(21) Appl. No.: 14/892,146

(22) PCT Filed: May 12, 2014

(86) PCT No.: PCT/JP2014/062581
§ 371 (c)(1),
(2) Date: Nov. 18, 2015

(87) PCT Pub. No.: WO2014/192520
PCT Pub. Date: Dec. 4, 2014

(65) Prior Publication Data
US 2016/0089020 A1 Mar. 31, 2016

(30) Foreign Application Priority Data
May 30, 2013 (JP) .................... 2013-114354

(51) Int. Cl.
*A61B 3/10* (2006.01)
*A61B 3/14* (2006.01)
*A61B 3/00* (2006.01)

(52) U.S. Cl.
CPC ............ *A61B 3/102* (2013.01); *A61B 3/0025* (2013.01); *A61B 3/0041* (2013.01); *A61B 3/0058* (2013.01); *A61B 3/14* (2013.01)

(58) Field of Classification Search
CPC .. A61B 3/10; A61B 3/00; A61B 3/102; A61B 3/0041; A61B 3/14; A61B 3/0025;
(Continued)

(56) References Cited

U.S. PATENT DOCUMENTS 6,377,349 B1    4/2002   Fercher
2006/0100528 A1   5/2006   Chan et al.
(Continued)

FOREIGN PATENT DOCUMENTS

JP    H09-276232 A    10/1997
JP    H11-325849 A    11/1999
(Continued)

OTHER PUBLICATIONS

International Search Report—PCT/JP2014/062581, dated Aug. 12, 2014.
(Continued)

*Primary Examiner* — Jie Lei
(74) *Attorney, Agent, or Firm* — Procopio, Cory, Hargreaves & Savitch LLP

(57) ABSTRACT

An embodiment provides a new technique of ophthalmologic diagnostic imaging. An ophthalmologic imaging apparatus of an embodiment includes: an acquiring part configured to acquire three-dimensional image data of an eye by using optical coherence tomography; a designating part configured for designating partial image data that is a part of the three-dimensional image data corresponding to a specific site of the eye; a deforming part configured to deform the three-dimensional image data such that the partial image data is deformed into a predetermined shape to create new three-dimensional image data; a forming part configured to form cross-sectional image data based on the new three-
(Continued)

dimensional image data; and a display controller configured to display an image based on the cross-sectional image data on a display means.

18 Claims, 11 Drawing Sheets

(58) Field of Classification Search
CPC ....... A61B 3/0058; A61B 3/103; A61B 3/152; A61B 3/113; A61B 3/107; A61B 3/04; A61B 3/1225; A61B 3/1015
USPC ....... 351/206, 205, 208, 210, 212, 216, 221, 351/236, 246; 600/425, 476
See application file for complete search history.

(56) References Cited

U.S. PATENT DOCUMENTS

| | | |
|---|---|---|
| 2007/0070295 A1 | 3/2007 | Tsukuda et al. |
| 2010/0220914 A1 | 9/2010 | Iwase et al. |
| 2011/0051088 A1 | 3/2011 | Shimizu et al. |
| 2012/0057127 A1 | 3/2012 | Iwase et al. |
| 2013/0093870 A1 | 4/2013 | Shibutani |
| 2014/0016096 A1 | 1/2014 | Iwase et al. |

FOREIGN PATENT DOCUMENTS

| | | |
|---|---|---|
| JP | 2002-139421 A | 5/2002 |
| JP | 2006-153838 A | 6/2006 |
| JP | 2007-024677 A | 2/2007 |
| JP | 2007-117714 A | 5/2007 |
| JP | 2008-073099 A | 4/2008 |
| JP | 2008259544 A | 10/2008 |
| JP | 2009011381 A | 1/2009 |
| JP | 2009-279031 A | 12/2009 |
| JP | 2010-200918 A | 9/2010 |
| JP | 2011-019644 A | 2/2011 |
| JP | 2011-045675 A | 3/2011 |
| JP | 2012-100811 A | 5/2012 |
| JP | 2012-161595 A | 8/2012 |

OTHER PUBLICATIONS

Notification of Reasons for Refusal for JP App No. 2016-143944 dated Apr. 3, 2018, 6 pgs.
Notification of Reasons for Refusal for JP App No. 2016-143945 dated Apr. 3, 2018, 7 pgs.

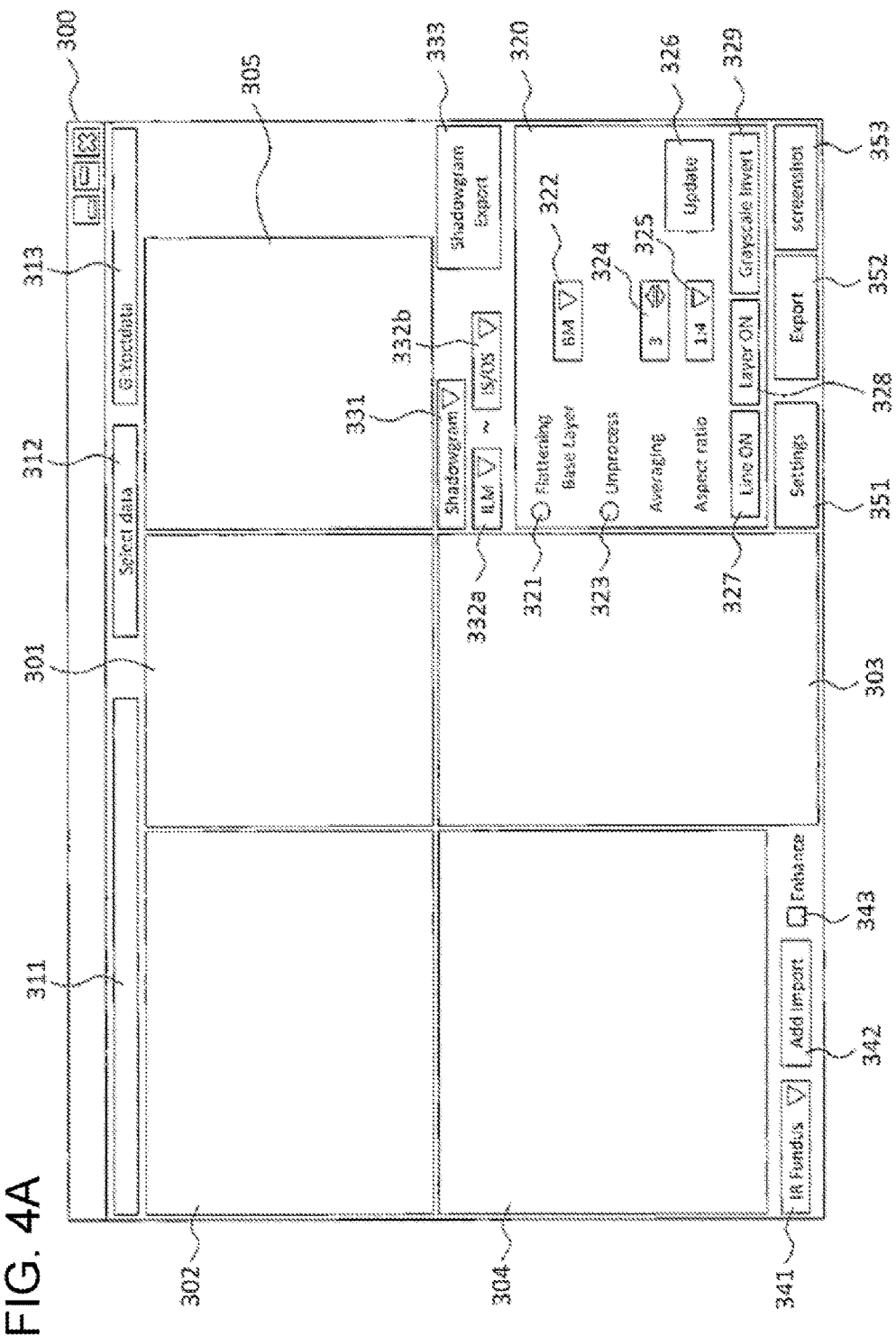

OPHTHALMOLOGIC IMAGING APPARATUS AND OPHTHALMOLOGIC IMAGE DISPLAY APPARATUS

STATEMENT REGARDING PRIOR DISCLOSURES BY THE INVENTORS UNDER 37 CFR 1.77(b)(6)

The subject matter of the instant application was disclosed by the inventors at the $51^{st}$ Japan Retina and Vitreous Society annual meeting on Dec. 1, 2012 at the Kofu Fujiya Hotel (Kofu, Yamanashi Prefecture, 3-2-30 Yumura).

TECHNICAL FIELD

The present invention relates to an ophthalmologic imaging apparatus that acquires an image of an eye using optical coherence tomography (OCT) and an ophthalmologic image display apparatus that displays an image of an eye acquired using OCT.

BACKGROUND TECHNOLOGY

In recent years, OCT has attracted attention which forms an image that represents surface and/or internal morphologies of an object using light beams from a laser light source etc. Unlike X-ray CT, OCT is noninvasive to human bodies and is therefore expected to be utilized in medical and biological fields in particular. For example, in ophthalmology, apparatuses for forming images of a fundus, a cornea, etc. are in practical stages.

An apparatus disclosed in Patent Document 1 uses so-called "Fourier Domain OCT" technique. More specifically, this apparatus irradiates an object with low-coherence light beam, superposes its reflected light and reference light to generate interference light, and acquires spectral intensity distribution of the interference light, and executes Fourier transform to form an image that represents morphology of the object in a depth direction (z-direction). Further, this apparatus is provided with a galvano mirror for scanning light beams (signal light) along one direction (x-direction) perpendicular to the z-direction, and with this, forms an image of a desired measurement targeted region of the object. An image formed by this apparatus is a two-dimensional cross-sectional image along the depth direction (z-direction) and scanning direction (x-direction) of the light beam. Such a technique is specifically called Spectral Domain.

Patent Document 2 discloses a technique that scans signal light in horizontal and vertical directions (x-direction and y-direction) to form a plurality of two-dimensional cross-sectional images along the horizontal direction, and acquires three-dimensional cross-sectional information of a measured area based on these cross-sectional images to perform imaging. Such three-dimensional imaging techniques include, for example: a method of arranging and displaying a plurality of cross-sectional images (referred to as stack data etc.); a method of generating volume data (voxel data) based on stack data, performing rendering on the volume data to form a three-dimensional image; and the like.

Patent Documents 3 and 4 disclose other types of OCT. An apparatus disclosed in Patent Document 3 scans wavelengths of light irradiated to an object (wavelength sweeping), detects interference light obtained by superposing reflected lights of the respective wavelengths on reference light to acquire spectral intensity distribution, and executes Fourier transform on it to image morphology of an object. Such an apparatus is called Swept Source type etc. Swept Source is a kind of Fourier Domain.

An apparatus disclosed in Patent Document 4 irradiates an object with light with predetermined beam diameter, and analyzes components of interference light obtained by superposing reflected light thereof and reference light to form an image of the object in a cross section orthogonal to traveling direction of the light. Such an apparatus is called Full-Field type, En-face type, or the like.

Patent Document 5 discloses an example of OCT application to ophthalmology. Before OCT was utilized, a retinal camera, a slit lamp microscope, a scanning laser ophthalmoscope (SLO) etc. were used for observing eyes (see Patent Documents 6 to 8 for example). A retinal camera photographs a fundus by irradiating an eye with illumination light and receiving reflected light thereof from the fundus. A slit lamp microscope obtains a cross-sectional image of a cornea by cutting off a light section of the cornea using slit light. An SLO images morphology of a retinal surface by scanning the fundus with laser light and detecting reflected light thereof using high-sensitive elements such as a photomultiplier.

OCT apparatuses have advantages over retinal cameras etc. in that a high-definition image may be obtained, a cross-sectional image and a three-dimensional image may be obtained, and the like.

In this way, OCT apparatuses can be used for observing various sites of an eye and is capable of obtaining a high-definition image; therefore, they have been utilized for diagnoses of various ophthalmologic disorders.

PRIOR ART DOCUMENTS

Patent Documents

[Patent Document 1] Japanese Unexamined Patent Application Publication No. H11-325849
[Patent Document 2] Japanese Unexamined Patent Application Publication No. 2002-139421
[Patent Document 3] Japanese Unexamined Patent Application Publication No. 2007-24677
[Patent Document 4] Japanese Unexamined Patent Application Publication No. 2006-153838
[Patent Document 5] Japanese Unexamined Patent Application Publication No. 2008-73099
[Patent Document 6] Japanese Unexamined Patent Application Publication No. H09-276232
[Patent Document 7] Japanese Unexamined Patent Application Publication No. 2008-259544
[Patent Document 8] Japanese Unexamined Patent Application Publication No. 2009-11381

SUMMARY OF THE INVENTION

Problems to be Solved by the Invention

In diagnostic imaging, observation and analysis of an eye from a variety of viewpoints are required. For example, not only cross-sectional images of a cornea or a fundus along the depth direction (z-direction) but also cross-sectional images in the transverse directions (xy-directions), cross-sectional images in an arbitrary direction, and the like are desired. Further, there are cases in which observation of an eye is performed while paying attention to a specific site and relationship between the specific site and another site is taken into consideration. As a concrete example, there is a case in which while paying attention to a specific layer of a retina, the shape of another layer standardized by the specific layer, the distance between another layer and the specific layer, and the like are desired.

A purpose of the present invention is to provide a new technique of ophthalmologic diagnostic imaging.

Means for Solving the Problem

An embodiment is an ophthalmologic imaging apparatus comprising: an acquiring part configured to acquire three-dimensional image data of an eye by using optical coherence tomography; a designating part configured for designating partial image data that is a part of the three-dimensional image data corresponding to a specific site of the eye; a deforming part configured to deform the three-dimensional image data such that the partial image data is deformed into a predetermined shape to create new three-dimensional image data; a forming part configured to form cross-sectional image data based on the new three-dimensional image data; and a display controller configured to display an image based on the cross-sectional image data on a display means.

EFFECT OF THE INVENTION

According to the present invention, it is possible to provide a new technique of ophthalmologic diagnostic imaging.

BRIEF DESCRIPTION OF THE DRAWINGS

FIG. 4A is a schematic diagram for illustrating an operation example of an ophthalmologic imaging apparatus according to an embodiment.

DETAILED DESCRIPTION

Examples of embodiments of an ophthalmological imaging apparatus and an ophthalmological image display apparatus according to the present invention are described in detail with reference to drawings. An ophthalmologic imaging apparatus according to an embodiment uses OCT to form an image of an eye. In the description, images acquired by OCT are sometimes referred to as OCT images. Further, measurement actions for forming OCT images are sometimes referred to as OCT measurement. In the description, "image data" and an "image" based on it are sometimes identified with each other.

In the following embodiments, configurations using Spectral Domain OCT are described in detail, particularly; however, configurations according to the embodiments may be applied to ophthalmologic imaging apparatuses using OCT of another type (such as Swept Source type). The following embodiments describe apparatuses that are combinations of OCT apparatus and retinal camera in detail, particularly; however, an imaging apparatus other than a retinal camera (such as an SLO, a slit lamp microscope, an ophthalmologic operation microscope, etc.) may be combined with an OCT apparatus including a configuration according to the embodiment. Alternatively, configurations according to the embodiments may be integrated into an OCT apparatus. The following embodiments describe cases of imaging a fundus (a retina, a choroid, a sclera) in detail, particularly; however, imaging targets are not so limited. For example, configurations according to the embodiments may be applied to an ophthalmologic imaging apparatus including an OCT apparatus that is capable of imaging arbitrary sites of an eye such as a vitreous body, a cornea, an iris, a crystalline lens, etc. The contents described in the documents cited in this description and any known technology may be applied to the following embodiments.

[Configurations]

Figure 1:
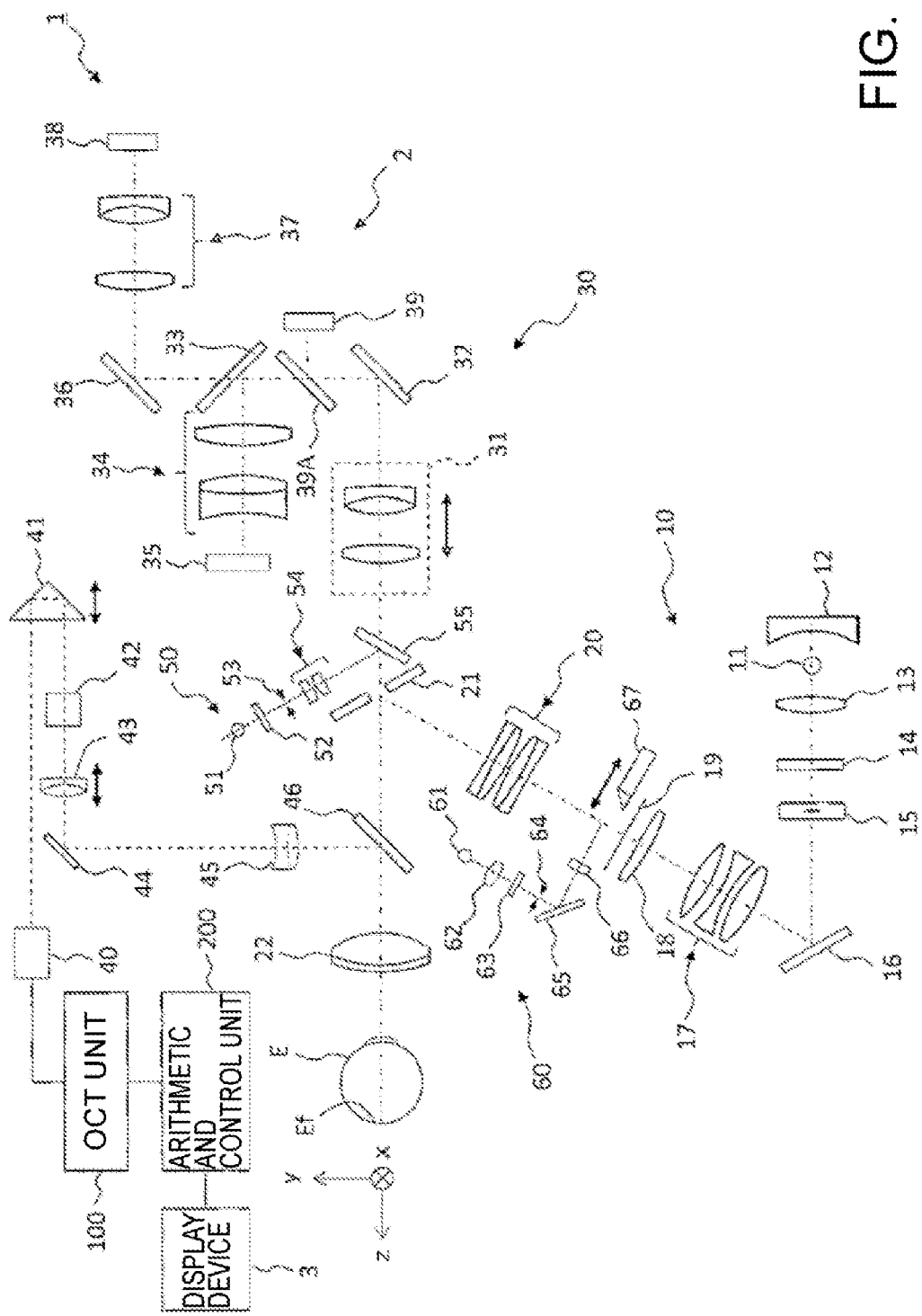
FIG. 1 is a schematic diagram illustrating a configuration example of an ophthalmologic imaging apparatus according to an embodiment.
Figure 2:
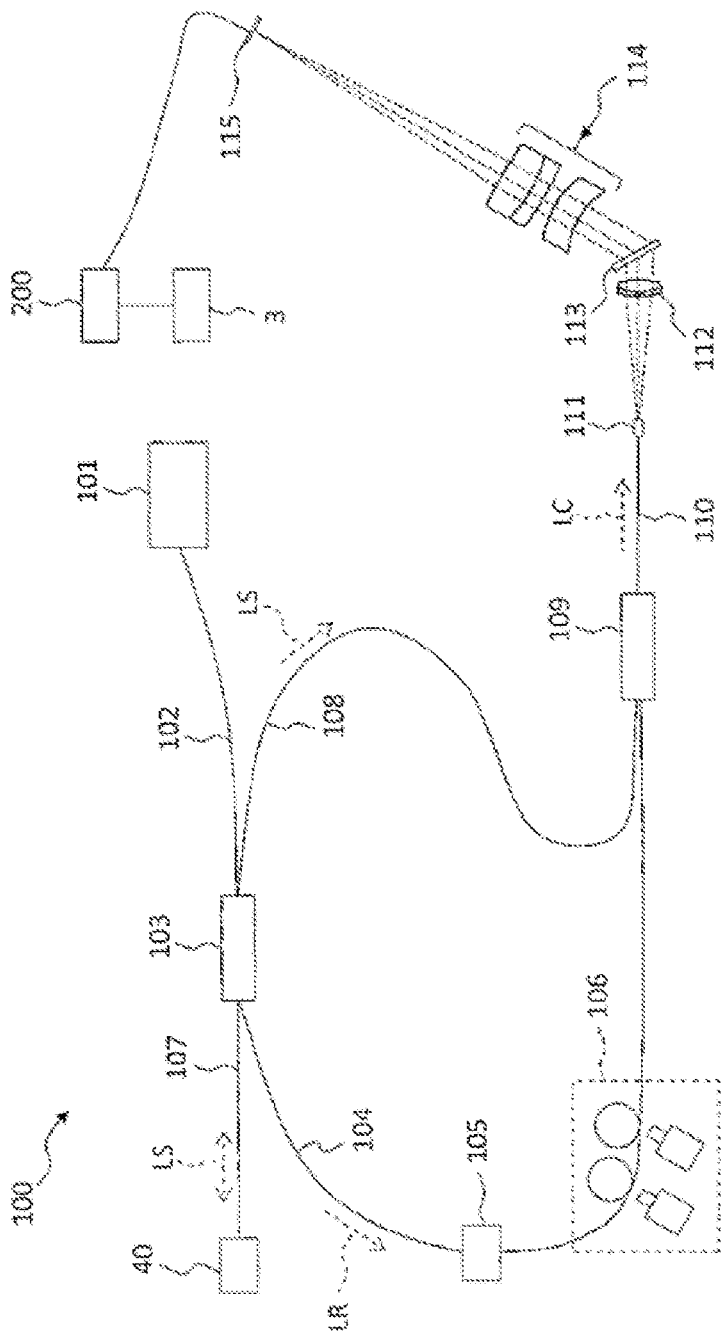
FIG. 2 is a schematic diagram illustrating a configuration example of an ophthalmologic imaging apparatus according to an embodiment.

As shown in FIG. 1 and FIG. 2, an ophthalmologic imaging apparatus 1 includes a retinal camera unit 2, an OCT unit 100 and an arithmetic and control unit 200. The retinal camera unit 2 includes almost the same optical systems as a conventional retinal camera. The OCT unit 100 is provided with optical systems for obtaining fundus OCT images. The arithmetic and control unit 200 includes a computer that executes various arithmetic processing, control processing, etc.

[Retinal Camera Unit]

The retinal camera unit 2 shown in FIG. 1 is provided with an optical system for obtaining two-dimensional images (fundus images) representing surface morphology of a fundus Ef of an eye E. Fundus images include observation images, photographed images, etc. An observation image is, for example, a monochromatic moving image formed at a predetermined frame rate using near-infrared light. A photographed image may be, for example, a color image captured by flashing visible light or a monochromatic still image captured using near-infrared light or visible light as illumination light. The retinal camera unit 2 may capture images of other types such as fluorescein angiography images, indocyanine green fluorescent images, autofluorescent images, and the like. Image data of any fundus image obtained by the retinal camera unit 2 is an example of "front image data". The retinal camera unit 2 is an example of a "photographing part". The "photographing part" may be a unit having a function other than a retinal camera such as a function as an SLO or a slit lamp microscope.

The retinal camera unit 2 is provided with a chin rest and forehead placement for supporting a subject's face. Moreover, the retinal camera unit 2 is provided with an illumination optical system 10 and a photographing optical system 30. The illumination optical system 10 irradiates the fundus Ef with illumination light. The photographing optical system 30 guides reflected light of illumination light from the fundus Ef to imaging devices (CCD image sensors 35 and 38 (sometimes referred to simply as CCD)). Further, the photographing optical system 30 guides signal light from the OCT unit 100 to the fundus Ef and guides the signal light returned from the fundus Ef to the OCT unit 100.

An observation light source 11 of the illumination optical system 10 includes a halogen lamp or an LED (Light Emitting Diode), for example. Light output from the observation light source 11 (observation illumination light) is reflected by a reflection mirror 12 with a curved reflection surface, passes through a condenser lens 13 and becomes near-infrared light after passing through a visible cut filter 14. Further, the observation illumination light is once focused at the vicinity of a photographing light source 15, reflected by a mirror 16 and passes through relay lenses 17 and 18, a diaphragm 19 and a relay lens 20. Then, the observation illumination light is reflected by a peripheral part (region surrounding an aperture part) of an aperture mirror 21, transmitted through a dichroic mirror 46 and refracted by an objective lens 22, thereby illuminating the fundus Ef.

The fundus-reflected light of the observation illumination light is refracted by the objective lens 22, transmitted through the dichroic mirror 46, passes through the aperture part formed in the center region of the aperture mirror 21, transmitted through a dichroic mirror 55, travels through a focusing lens 31 and reflected by a mirror 32. Further, the fundus-reflected light is transmitted through a half-mirror 39A, reflected by a dichroic mirror 33 and forms an image on a light-receiving surface of the CCD 35 by a condenser lens 34. The CCD 35 detects the fundus-reflected light at a preset frame rate, for example. An image (observation image) based on the fundus-reflected light detected by the CCD 35 is displayed on a display device 3. When focus of the photographing optical system 30 is adjusted on an anterior eye part, an observation image of the anterior eye part of the eye E is displayed.

The photographing light source 15 includes a xenon lamp or an LED, for example. Light output from the photographing light source 15 (photographing illumination light) is irradiated to the fundus Ef through the same route as that of the observation illumination light. Fundus-reflected light of the photographing illumination light is guided to the dichroic mirror 33 via the same route as that of the observation illumination light, transmitted through the dichroic mirror 33, reflected by a mirror 36 and forms an image on a light-receiving surface of the CCD 38 by a condenser lens 37. An image based on the fundus-reflected light detected by the CCD 38 (photographed image) is displayed on the display device 3. The display device 3 on which observation images are displayed and the display device 3 on which the photographed images are displayed may be the same or different. When similar photography is performed by illuminating the eye E with infrared light, an infrared photographed image is displayed.

An LCD (Liquid Crystal Display) 39 displays a fixation target, a target for a visual-acuity test, etc. The fixation target is a visual target for fixating the eye E and used for fundus photography, OCT, etc.

Part of light output from the LCD 39 is reflected by the half-mirror 39A, reflected by the mirror 32, travels through the focusing lens 31 and the dichroic mirror 55, passes through the aperture part of the aperture mirror 21, transmitted through the dichroic mirror 46, refracted by the objective lens 22, and projected onto the fundus Ef.

By changing a display position of the fixation target on the LCD 39's screen, a fixation position of the eye E can be changed. Examples of fixation positions of the eye E include a position for acquiring an image centered at a macula of the fundus Ef, a position for acquiring an image centered at an optic disc, a position for acquiring an image centered at a fundus center located between the macula and the optic disc, etc., as in conventional retinal cameras. Further, the display position of the fixation target can be changed arbitrarily.

As with conventional retinal cameras, the retinal camera unit 2 includes an alignment optical system 50 and a focus optical system 60. The alignment optical system 50 generates a target (alignment index) for matching the position of the optical system with the eye E (that is, for performing alignment). The focus optical system 60 generates a target (split index) for adjusting focus with respect to the fundus Ef.

Light output from an LED 51 of the alignment optical system 50 (alignment light) passes through diaphragms 52 and 53 and a relay lens 54, is reflected by the dichroic mirror 55, passes through the aperture part of the aperture mirror 21, is transmitted through the dichroic mirror 46 and is projected on the cornea of the eye E by the objective lens 22.

Cornea-reflected light of the alignment light passes through the objective lens 22, the dichroic mirror 46 and the aperture part, and then part of the cornea-reflected light is transmitted through the dichroic mirror 55, passes through the focusing lens 31, reflected by the mirror 32, transmitted through the half-mirror 39A, reflected by the dichroic mirror 33, and projected on the light-receiving surface of the CCD 35 by the condenser lens 34. An image captured by the CCD 35 (alignment index) is displayed on the display device 3 together with the observation image. The user performs the same operation as conventional retinal cameras to conduct alignment. The arithmetic and control unit 200 may perform alignment by analyzing the position of the alignment index and moving the optical system (automatic alignment).

When performing focus adjustment, a reflection surface of a reflection rod 67 is obliquely disposed in an optical path of the illumination optical system 10. Light output from an LED 61 of the focus optical system 60 (focus light) passes through a relay lens 62, is split into two light fluxes by a split index plate 63, passes through a two-hole diaphragm 64, is reflected by a mirror 65, is formed an image on the reflection surface of the reflection rod 67 by a condenser lens 66 and is reflected. Further, the focus light passes through the relay lens 20, is reflected by the aperture mirror 21, is transmitted through the dichroic mirror 46, is refracted by the objective lens 22 and is projected on the fundus Ef.

Fundus-reflected light of the focus light passes through the same route as that of the cornea-reflected light of the alignment light and is detected by the CCD 35. An image captured by the CCD 35 (split index) is displayed on the display device 3 together with the observation image. The arithmetic and control unit 200 performs focus adjustment by analyzing the position of the split index and moving the focusing lens 31 and the focus optical system 60 as in a conventional way (automatic focusing). The user can conduct focus adjustment by hand while observing the split index.

An optical path for OCT is branched from an optical path for fundus photography by the dichroic mirror 46. The dichroic mirror 46 reflects light of wavelength bands for OCT and transmits light for fundus photography. The OCT optical path includes a collimator lens unit 40, an optical path length changing part 41, a galvano scanner 42, a focusing lens 43, a mirror 44 and a relay lens 45 in this order from the OCT unit 100.

The optical path length changing part 41 is movable in a direction indicated by an arrow in FIG. 1 to change optical path length of the OCT optical path. Change in the optical path length may be used for correction of the optical path length according to an axial length of the eye E, adjustment of an interference state, etc. The optical path length changing part 41 includes a corner cube and a mechanism that moves the corner cube, for example.

The galvano scanner 42 changes a traveling direction of light (signal light LS) guided along the OCT optical path. Accordingly, the fundus Ef is scanned by the signal light LS. The galvano scanner 42 includes a galvano mirror for deflecting the signal light LS in the x-direction, a galvano mirror for deflecting the signal light LS in the y-direction, and a mechanism for independently driving the galvano mirrors. With such a configuration, the signal light LS is deflected in an arbitrary direction in the xy-plane.

[OCT Unit]

An example of a configuration of the OCT unit 100 is explained with reference to FIG. 2. The OCT unit 100 is provided with an optical system for obtaining OCT images of the fundus Ef. This optical system includes a configuration similar to a conventional Spectral Domain OCT apparatus. Specifically, this optical system is configured to split low-coherence light into signal light and reference light, superpose the signal light returned form the fundus Ef with the reference light having traveled through a reference light path to generate interference light, and detect spectral components of the interference light. The result of the detection (detection signals) is transmitted to the arithmetic and control unit 200.

When Swept Source OCT is applied, a wavelength-sweeping light source (wavelength tunable light source) is provided instead of a low-coherence light source and an optical member for spectrally decomposing interference light is not provided. In general, regarding a configuration of the OCT unit 100, any known technology according to the type of OCT may be appropriately applied.

A light source unit 101 outputs broadband, low-coherence light L0. The low-coherence light L0, for example, contains near-infrared wavelength bands (about 800-900 nm) and has a temporal coherence length of about tens of micrometer. The low-coherence light L0 may be near-infrared light of wavelength bands invisible for human eyes such as near-infrared light having center wavelength of about 1040-1060 nm.

The light source unit 101 includes light-emitting device, such as an SLD (super luminescent diode), an LED, an SOA (Semiconductor Optical Amplifier), or the like.

The low-coherence light L0 output from the light source unit 101 is guided to a fiber coupler 103 through an optical fiber 102, and split into signal light LS and reference light LR.

The reference light LR is guided to an optical attenuator 105 through an optical fiber 104. The optical attenuator 105 automatically adjusts light quantity of the reference light LR guided through the optical fiber 104 under control of the arithmetic and control unit 200 by using any known technology. The light quantity of the reference light LR is adjusted by the optical attenuator 105, and then the reference light LR is guided through the optical fiber 104 and reaches a polarization controller 106. The polarization controller 106 applies stress from outside to the optical fiber 104 in loop shape to change a polarization state of the reference light LR guided through the optical fiber 104, for example. A configuration of the polarization controller 106 is not limited to this and arbitrary known technology may be applied to it. The polarization state of the reference light LR is adjusted by the polarization controller 106, and then the reference light LR is guided to an optical coupler 109.

The signal light LS generated by the fiber coupler 103 is guided through the optical fiber 107 and converted into a parallel light flux by the collimator lens unit 40. Further, the signal light LS travels through the optical path length changing part 41, the galvano scanner 42, the focusing lens 43, the mirror 44 and the relay lens 45, and reaches the dichroic mirror 46. Then, the signal light LS is reflected by the dichroic mirror 46, refracted by the objective lens 22 and projected onto the fundus Ef. The signal light LS is scattered (and reflected) at various depth positions of the fundus Ef. Back-scattered light of the signal light LS from the fundus Ef travels along the same route as the outward way in the opposite direction to the fiber coupler 103, and reaches the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Further, the interference light LC is converted into a parallel light flux by a collimator lens 112, spectrally divided (spectrally decomposed) by a diffraction grating 113, converged by a condenser lens 114, and projected onto a light-receiving surface of a CCD image sensor 115. Although the diffraction grating 113 shown in FIG. 2 is of transmission type, any other kinds of spectrally decomposing elements (such as reflection type) may be used.

The CCD image sensor 115 is for example a line sensor, and detects respective spectral components of the spectrally-decomposed interference light LC and converts the detected components into electric charges. The CCD image sensor 115 accumulates the electric charges to generate detection signals and transmits the detection signals to the arithmetic and control unit 200. When Swept Source OCT is applied, a balanced photodetector such as a balanced photodiode is provided instead of a CCD image sensor.

Although Michelson-type interferometer is employed in the embodiment, any type of interferometer such as a Mach-Zehnder-type may be employed as necessary. Instead of a CCD image sensor, an image sensor of another type such as a CMOS (Complementary Metal Oxide Semiconductor) image sensor may be used.

[Arithmetic and Control Unit]

A configuration of the arithmetic and control unit 200 is described. The arithmetic and control unit 200 analyzes detection signals input from the CCD image sensor 115 to form an OCT image of the fundus Ef. Arithmetic processing for this is the same as a conventional Spectral Domain OCT apparatus.

The arithmetic and control unit 200 controls each part of the retinal camera unit 2, the display device 3 and the OCT unit 100. For example, the arithmetic and control unit 200 displays the OCT image of the fundus Ef on the display device 3.

As controls for the retinal camera unit 2, the arithmetic and control unit 200 executes: action controls of the observation light source 11, the photographing light source 15 and the LED's 51 and 61; action control of the LCD 39; movement controls of the focusing lenses 31 and 43; movement control of the reflection rod 67; movement control of the focus optical system 60; movement control of the optical path length changing part 41; action control of the galvano scanner 42; and the like.

As controls for the OCT unit 100, the arithmetic and control unit 200 executes: action control of the light source unit 101; action control of the optical attenuator 105; action control of the polarization controller 106; action control of the CCD image sensor 115; and the like.

The arithmetic and control unit 200 includes a microprocessor, a RAM, a ROM, a hard disk drive, a communication interface, etc. as with a conventional computer. Storage devices such as a hard disk drive store computer programs for controlling the ophthalmologic imaging apparatus 1. The arithmetic and control unit 200 may include various circuit boards such as circuit boards for OCT-image formation. The arithmetic and control unit 200 may include operation devices (input devices) such as a keyboard and a mouse and/or a display device such as an LCD.

The retinal camera unit 2, the display device 3, the OCT unit 100 and the arithmetic and control unit 200 may be integrally configured (that is, may be provided within a single case) or separately configured in two or more cases.

[Control System]

A configuration of a control system of the ophthalmologic imaging apparatus 1 is described with reference to FIG. 3.

(Controller)

A controller 210 is the center of the control system of the ophthalmologic imaging apparatus 1. The controller 210 includes the aforementioned microprocessor, RAM, ROM, hard disk drive and communication interface, etc., for example. The controller 210 includes a main controller 211 and storage 212.

(Main Controller)

The main controller 211 performs various controls as described above. In particular, the main controller 211 controls a focus driver 31A, the optical path length changing part 41 and the galvano scanner 42 in the retinal camera unit 2 as well as the light source unit 101, the optical attenuator 105 and the polarization controller 106 in the OCT unit 100.

The focus driver 31A moves the focusing lens 31 in a direction of the optical axis. With this, a focus position of the photographing optical system 30 is varied. The main controller 211 may control an optical system driver to three-dimensionally move the optical systems provided in the retinal camera unit 2. Such control is used for alignment and tracking. Tracking is an operation to move the optical systems in accordance with eye movement of the eye E. When tracking is performed, alignment and focus adjustment are performed in advance. Tracking is a function to maintain suitable positional relationship in which alignment and focusing are matched by changing the positions of the optical systems to follow eye movement.

The main controller 211 writes data into the storage 212 and reads out data from the storage 212. The main controller 211 displays a variety of information on the display 241. The main controller 211 functions as a "display controller".

(Storage)

The storage 212 stores various kinds of data. Data stored in the storage 212 includes OCT image data, fundus image data, eye information, for example. The eye information includes information regarding subjects such as patient ID's and names, and information regarding eyes such as identification of left/right eye. The storage 212 stores various kinds of programs and data for operating the ophthalmologic imaging apparatus 1.

(Image Forming Part)

An image forming part 220 forms cross-sectional image data of the fundus Ef based on detection signals from the CCD image sensor 115. This processing includes noise elimination (noise reduction), filtering, dispersion compensation, FFT (Fast Fourier Transform), etc. like conventional Spectral Domain OCT. The cross-sectional image data thus formed includes a plurality of one-dimensional image data (A-line data) which extends in the z-direction from a plurality of scanning points on a scanning line(s). Each A-line data is assigned with the xy-coordinate values of the position of the corresponding scanning point.

When an OCT apparatus of another type is employed, the image forming part 220 executes known processing in accordance with the type. The image forming part 220 may include the aforementioned circuit boards, for example.

(Image Processor)

An image processor 230 executes various kinds of image processing and analysis on images formed by the image forming part 220. For example, the image processor 230 executes various kinds of corrections such as brightness correction of images etc. Moreover, the image processor 230 executes various kinds of image processing and analysis on images obtained by the retinal camera unit 2 (fundus images, anterior eye part images, etc.).

The image processor 230 includes a three-dimensional image data forming part 231, a partial image data designating part 232, an image data deforming part 233 and a cross-sectional image data forming part 234. The three-dimensional image data forming part 231 functions as an "acquiring part" together with the optical systems used for OCT measurement and the image forming part 220. The partial image data designating part 232 functions as a "designating part". The image data deforming part 233 functions as a "deforming part". The cross-sectional image data forming part 234 functions as a "forming part".

(Three-dimensional Image Data Forming Part)

The three-dimensional image data forming part 231 executes known image processing such as interpolation that interpolates pixels between cross-sectional images acquired along a plurality of scanning line, thereby forming three-dimensional image data of the fundus Ef. Three-dimensional image data refers to image data in which pixel positions are defined by a three-dimensional coordinate system. An example of three-dimensional image data is image data composed of three-dimensionally arranged voxels. Such image data is referred to as volume data, voxel data, etc.

In order to display an image based on volume data, the image processor 230 (the cross-sectional image data forming part 234) executes rendering processing (such as volume rendering, MPR (Multi Planar Reconstruction), MIP (Maximum Intensity Projection), etc.) on the volume data to form image data of a pseudo three-dimensional image taken from a specific view direction. The pseudo three-dimensional image is displayed on a display device such as a display 241.

The three-dimensional image data may be stack data of a plurality of cross-sectional image. Stack data is image data formed by three-dimensionally arranging a plurality of cross-sectional images acquired along a plurality of scanning lines, wherein the arrangement is based on positional relationship of the scanning lines. That is, stack data is image data obtained by representing, with a single three-dimensional coordinate system, cross-sectional images originally defined by individual two-dimensional coordinate systems (in other words, by embedding them into a single three-dimensional space).

(Partial Image Data Designating Part)

The partial image data designating part 232 executes processing for designating partial image data that is a part of the three-dimensional image data corresponding to a specific site of the eye E.

The specific site of the eye E is a site to be a standard in image data deformation in a post stage. The specific site may be an arbitrary site of the eye E.

When imaging an eye fundus like the present embodiment, the specific site may be any of the following eye sites.

Layer tissues in a retina: inner limiting membrane, nerve fiber layer, ganglion cell layer, inner plexiform layer, inner nuclear layer, outer plexiform layer, outer nuclear layer, external limiting membrane, photoreceptor layer, retinal pigment epithelium Tissues neighboring a retina: Bruch membrane, choroid, sclera, vitreous body (Cloquet' canal, vitreous pocket), cribrosa lamina Boundaries of tissues: NFL/GCL (nerve fiber layer/ganglion cell layer boundary), IPL/INL (inner plexiform layer/inner nuclear layer boundary), IS/OS (inner segment/outer segment junction), CSI (choroid/sclera interface)

When imaging an anterior eye segment, the specific site may be layer tissues in a cornea (corneal epithelium, Bowman membrane, corneal stoma, Descemet membrane, corneal endothelium), an iris, a crystalline lens, and boundary between them.

The specific site of an eye may be a default setting or may be set for each examination. In the latter case, it is automatically set according to examination contents or manually set by the user, for example. In the case of a default setting automatic setting, the partial image data designating part 232 serves as the "designating part". In the case of manual setting, the partial image data designating part 232 and a user interface 240 serve as the "designating part".

An example of processing in the case of the default setting is described. The partial image data designating part 232 analyzes the three-dimensional image data to specify image areas corresponding to layer tissues and/or boundaries, and determines, from among the specified image areas, an image area corresponding to the specific site that is the default setting.

An example of processing in the case of the automatic setting is described. The partial image data designating part 232 specifies examination contents or the like based on an operation mode (examination mode or the like) of the ophthalmologic imaging apparatus 1 or an electronic medical record. The partial image data designating part 232 stores information in which examination contents or the like and specific sites are associated with each other in advance, and selects a specific site corresponding to the specified examination contents or the like based on this information. Further, the partial image data designating part 232 analyzes the three-dimensional image data to specify image areas corresponding to layer tissues and/or boundaries, and determines, from among the specified image areas, an image area corresponding to the selected specific site.

A first example of processing in the case of the manual setting is described. The image processor 230 (the cross-sectional image data forming part 234, for example) performs MPR processing to the three-dimensional image data created by the three-dimensional image data forming part 231 to form cross-sectional image data (standard cross-sectional image data) in a standard section substantially along a traveling direction of signal light LS irradiated to the eye E. Here, the standard cross-sectional image data may be any of a plurality of cross-sectional image data used for the formation of the three-dimensional image data. The formation of the standard cross-sectional image data based on the three-dimensional image data includes such processing.

The standard section may be any cross section along the z-direction in the three-dimensional image data. For example, the standard section is a cross section passing through the center position of the three-dimensional image data.

The main controller 211 displays a cross-sectional image (standard cross-sectional image) based on the standard cross-sectional image data on the display 241. The user designates an image area in the standard cross-sectional image using the operation part 242. This designation operation is performed by designating a position corresponding to a desired layer tissue or boundary in the standard cross-sectional image using a pointing device (mouse or the like), for example.

Based on the image area designated by the user, the partial image data designating part 232 analyzes the three-dimensional image data to perform designation of a partial image data. This designation processing is performed by expanding the image area designated in the standard cross-sectional image to the totality of the three-dimensional image data based on the pixel values (voxel values) of the three-dimensional image data, for example. In other words, this designation is processing of enlarging the image area corresponding to the specific site designated in the standard cross-sectional image (which is a two-dimensional image) to a data area corresponding to the specific site in the entire three-dimensional image data. Such processing is performed, for example, based on features of pixel values corresponding to the specific site, the shape of the specific site, positional relationship between the specific site and other sites, or the like.

A second example of processing in the case of the manual setting is described. The main controller 211 displays selection information in which a plurality of tissues of an eye is selectably presented on the display 241. An example of the selection information is a drop-down list in which names of a plurality of tissues of an eye is listed. The user selects a desired tissue from among the plurality of tissues presented in the selection information using the operation part 242. The partial image data designating part 232 analyzes the three-dimensional image data based on the selected tissue to specify a part of the three-dimensional image data corresponding to the selected tissue. This analysis is performed in the same way as in the first example, for example. The part of the three-dimensional image data thus specified is used as the partial image data.

In the present example, the following configuration may be optionally employed. First, the cross-sectional image data forming part 234 forms standard cross-sectional image data in the same way as in the case of the manual setting, and the main controller 211 displays a standard cross-sectional image based on the standard cross-sectional image data on the display 241. The user selects a desired tissue of the plurality of tissues presented in the selection information using the operation part 242. The main controller 211 changes a display aspect of a part of the standard cross-sectional image corresponding to the selected tissue. This display control processing is performed, for example, by displaying an image with a predetermined color (straight line image, sheet-like image over the part corresponding to the concerned tissue. Such overlay processing is performed using a layer function of an operating system, for example. The user can check the part whose display aspect is changed and determine whether the selection of the tissue is suitable.

If the selected tissue is not suitable, the user can select a tissue using the selection information again.

(Image Data Deforming Part)

The image data deforming part 233 deforms the three-dimensional image data formed by the three-dimensional image data forming part 231 such that the partial image data designated by the partial image data designating part 232 is deformed into a predetermined shape.

In the present embodiment, the partial image data is a two-dimensional area (a tissue or a boundary of tissues of an eye fundus) in three-dimensional image data. In this case, the image data deforming part 233 is capable of performing deformation of the three-dimensional image data such that a two-dimensional area corresponding to the partial image data is deformed into a planar shape. This deformation processing is performed, for example, by shifting sequences of voxels on A-lines in the z-direction such that the z-coordinate values of voxels corresponding to the partial image data become the same.

In another example of deformation processing, the image data deforming part 233 is capable of performing deformation of the three-dimensional image data such that a two-dimensional area corresponding to the partial image data is deformed into a curved shape. Examples of such curved shapes include shapes as default settings, shape preset according to examination contents or the like, shapes preset according to kinds of specific sites (names of tissues or the like), shapes arbitrarily set by users, and the like. This deformation processing is performed, for example, by shifting sequences of voxels on A-lines in the z-direction such that the z-coordinate values of voxels corresponding to the partial image data are arranged in an aimed curved shape.

The partial image data may be a three-dimensional area in three-dimensional image data. In this case, the image data deforming part 233 performs deformation of three-dimensional image data such that the three-dimensional area is deformed into a predetermined shape.

It is not necessary that the image data deforming part 233 deforms the entirety of three-dimensional image data. For example, the image data deforming part 233 is capable of a partial area of the three-dimensional image data that includes at least the partial image data.

(Cross-sectional Image Data Forming Part)

The cross-sectional image data forming part 234 forms cross-sectional image data based on the three-dimensional image data deformed by the image data deforming part 233 (deformed three-dimensional image data). This processing is performed, for example, by applying MPR processing or the like to the deformed three-dimensional image data. As described above, the cross-sectional image data forming part 234 is capable of executing formation of cross-sectional image data based on the three-dimensional image data formed by the three-dimensional image data forming part 231, that is, based on the three-dimensional image data before deformation.

The image processor 230 that functions as above includes, for example, the aforementioned microprocessor, RAM, ROM, hard disk drive, circuit boards, and the like. Computer programs causing the microprocessor to realize the above functions are stored in storage devices such as the hard disk drive in advance.

(User Interface)

The user interface 240 includes the display 241 and the operation part 242. The display 241 includes a display device in the arithmetic and control unit 200 and/or the display device 3. The operation part 242 includes operation devices in the arithmetic and control unit 200. The operation part 242 may include various kinds of buttons, keys, and the like provided on the case of the ophthalmologic imaging apparatus 1 or outside thereof. For example, when the retinal camera unit 2 has a case similar to conventional retinal cameras, a joy stick, an operation panel and the like provided on the case are included in the operation part 242. The display 241 may include various display devices such as a touch panel or the like provided on the case of the retinal camera unit 2.

The display 241 and operation part 242 are not necessarily separate components. For example, like a touch panel, a compound device of a display function and an operation function may be used. In this case, the operation part 242 includes the touch panel and computer programs. Contents of operation to the operation part 242 are input into the controller 210 as electrical signals. Further, operations and/or information input may be performed by means of graphical user interface (GUI) displayed on the display 241 and the operation part 242.

[Scanning of Signal Light and OCT Images]

Now, scanning of the signal light LS and OCT images are described.

Scanning modes of the signal light LS by the ophthalmologic imaging apparatus 1 may include, for example, line scan (horizontal scan, vertical scan), crossed scan, radial scan, circular scan, concentric scan, helical scan, etc. Taking observation sites of a fundus, analysis modes (retinal thickness etc.), time required for scanning, density of scanning, etc. into account, these scanning modes are selectively used.

In the horizontal scan, the signal light LS is scanned in the horizontal direction (x-direction). The horizontal scan includes a mode in which the signal light LS is scanned along a plurality of scanning lines extending in the horizontal direction and arranged in the vertical direction (y-direction). In this mode, the interval between scanning lines can be set arbitrarily. By setting the interval between adjacent scanning lines to be sufficiently narrow, three-dimensional image data may be formed (three-dimensional scan). The present embodiment uses the three-dimensional scan. The vertical scan is performed in a similar manner.

In the crossed scan, the signal light LS is scanned along a cross-shape trajectory consisting of two linear trajectories (linear trajectories) orthogonal to each other. In the radial scan, the signal light LS is scanned along a radial trajectory consisting of a plurality of linear trajectories arranged at predetermined angles. The crossed scan is an example of the radial scan.

In the circular scan, the signal light LS is scanned along a circular trajectory. In the concentric scan, the signal light LS is scanned along a plurality of circular trajectories arranged concentrically around a predetermined center position. The circular scan is an example of the concentric scan. In the helical scan, the signal light LS is scanned along a helical trajectory while making the turning radius gradually smaller (or greater).

Since the galvano scanner 42 is configured to scan the signal light LS in the directions orthogonal to each other, the signal light LS can be scanned in the x and y-directions independently. Further, the signal light LS can be scanned along an arbitrary trajectory on the xy-plane by simultaneously controlling the orientations of the two galvano mirrors included in the galvano scanner 42. With this, various kinds of scanning modes as described above can be realized.

By scanning the signal light LS in the modes described as above, it is possible to obtain a cross-sectional image data in a plane spanned by the direction along a scanning line and the depth direction (z-direction). Moreover, when the interval between scanning lines is narrow, three-dimensional image data can be obtained.

An area in the fundus Ef to be scanned by the signal light LS as described above, that is, an area in the fundus Ef subject to OCT is referred to as a scanning area. A scanning area of the three-dimensional scan is a rectangular area in which a plurality of horizontal scans is arranged. A scanning area of the concentric scan is a disciform area surrounded by the trajectory of the circular scan with maximum diameter. A scanning area of the radial scan is a disciform (or polygonal) area connecting ends of the scanning lines.

[Operation]

An operational example of the ophthalmologic imaging apparatus 1 is described. FIGS. 4A to 4D show display screens (windows) in the operational example.

(OCT Measurement)

Firstly, the face of the subject is fixed by means of the chin rest and the forehead placement. Then, the eye E is continuously illuminated with the illumination light from the observation light source 11 (this is near-infrared light through the visible cut filter 14), and acquisition of a near-infrared moving image of the eye E is commenced. The main controller 211 can store one or more frames of the near-infrared moving image in the storage 212.

Further, the main controller 211 controls the alignment optical system 50 to project the alignment index, controls the focus optical system 60 to project the split index, and controls the LCD 39 to project the fixation target on the eye E. Alignment and focus adjustment with respect to the eye E are performed using these indices.

OCT measurement of the fundus Ef by means of the OCT unit 100 is commenced. At first, the line scan of a predetermined site of the fundus Ef (the vicinity of the macula or the vicinity of the optic disc, for example) is repeatedly performed to acquire time series cross-sectional image data in a single section. The image processor 230 analyzes the cross-sectional image data to calculate a correction amount of the optical path length difference between the signal light LS and the reference light LR. The main controller 211 controls the optical path length changing part 41 based on the correction amount to adjust the focus for OCT measurement.

When a trigger of the start of OCT measurement is issued, the main controller 211 performs control for the three-dimensional scan of the fundus Ef (that is, line scans on a plurality of scanning lines). Based on detection signals acquired by the respective line scans, the image forming part 220 forms cross-sectional image data corresponding to the respective scanning lines. The three-dimensional image data forming part 231 forms three-dimensional image data representing a targeted area of three-dimensional scan based on a plurality of cross-sectional image data corresponding to the plurality of scanning lines formed by the image forming part 220.

As necessary, the main controller 211 controls the retinal camera unit 2 to photograph the fundus Ef. With this, a color image data of the fundus Ef or the like is acquired. The main controller 211 can store the color image data in the storage 212 as a front image data.

(Display Screen)

Diagnostic imaging software is stored in the storage 212 in advance. When a trigger of the start of the software is issued, the main controller 211 causes the diagnostic imaging software to start. FIG. 4A shows an example of a screen thereby displayed.

A window 300 shown in FIG. 4A is provided with five image display parts 301 to 305. The display parts 301 to 305 are a transverse cross-sectional image display part, two longitudinal cross-sectional image display parts, a front image display part, and a processed image display part, respectively. Images based on the three-dimensional image data acquired in the prior stage are displayed in the transverse cross-sectional image display part 301, the longitudinal cross-sectional image display parts 302 and 303, and the processed image display part 305. An image based on the front image data acquired in the prior stage is displayed in the front image display part 304. Note that images displayed in the image display parts 301 to 305 are not so limited, and OCT images and fundus images of the eye E acquired by the ophthalmologic imaging apparatus 1 and other apparatuses in the past can be displayed in them.

In the transverse cross-sectional image display part 301, an image in the xy cross section orthogonal to the z-direction (also referred to as a C cross section) is displayed.

In each of the longitudinal cross-sectional image display parts 302 and 303, an image in a cross section along the z-direction (also referred to as a B cross section) is displayed. In each of the longitudinal cross-sectional image display parts 302 and 303, a B cross-sectional image according to arrangement relation with respect to the transverse cross-sectional image display part 301 is displayed. For example, if the horizontal direction of the window 300 corresponds to the x-direction in a C cross-sectional image displayed in the transverse cross-sectional image display part 301 and if the vertical direction corresponds to the y-direction, a B cross-sectional image in the yz cross section is displayed in the longitudinal cross-sectional image display part 302 that is located on the left side of the transverse cross-sectional image display part 301, and a B cross-sectional image in the xz cross section is displayed in the longitudinal cross-sectional image display part 303 that is located below the transverse cross-sectional image display part 301.

In the front image display part 304, an image based on the front image data as described above. Examples of images displayed in the front image display part 304 include a near-infrared moving image, a frame thereof (still image), a color image, and the like.

In the processed image display part 305, an image obtained by applying a predetermined processing to the three-dimensional image data (processed image) is displayed. Examples of processed images include feature enhanced image obtained by enhancing a desired feature site. Examples of feature enhanced images include a shadowgram. The shadowgram is formed by projecting data included in a predetermined z-range of the three-dimensional image data onto the z-direction. This processing is performed by the image processor 230.

In addition, the window shown in FIG. 4A is provided with a patient information display part 311, a data selecting part 312, and a data storage location display part 313. In the patient information display part 311, information regarding a patient such as a patient ID and a patient name is displayed. When the data selecting part 312 is clicked, a pop-up window for selecting three-dimensional image data to be observed is displayed. In the pop-up window, a list of information regarding three-dimensional image data included in folders that is previously set as storage locations of three-dimensional image data. The user selects desired three-dimensional image data from the list. Then, information on a folder in which the selected three-dimensional image data is stored is displayed in the data storage location display part 313.

Further, the window shown in FIG. 4A is provided with a processing content setting part 320. The processing content setting part 320 includes a deformation execution instructing part 321, a standard layer selecting part 322, a deformation nonexecution instructing part 323, an averaging range setting part 324, an aspect ratio setting part 325, an update button 326, a sectional position display switching part 327, a layer position display switching part 328, and a grayscale inverting part 329.

The processing content setting part 320 is provided with software keys for setting image processing. When deformation of three-dimensional image data is performed, the user clicks the deformation execution instructing part 321. On the other hand, when deformation of three-dimensional image data is not performed, the user clicks the deformation nonexecution instructing part 323. The deformation execution instructing part 321 and the deformation nonexecution instructing part 323 are alternatively operated. When the deformation execution instructing part 321 is selected, the user selects a desired item from the list of layer tissues and layer boundaries presented in the standard layer selecting part 322 configured as a drop-down list. A layer tissue or a layer boundary thus selected is used as the "specific site" described above. The list presented in the standard layer selecting part 322 is an example of the "selection information" described above.

The averaging range setting part 324 is used for setting a range (the number of pixels) of averaging executed in the formation of a C cross-sectional image. The user sets the range by operating up/down buttons provided in the averaging range setting part 324. The aspect ratio setting part 325 is used for setting the aspect ratio of a B cross-sectional image. The update button 326 is operated for reflecting contents set by the processing content setting part 320 in display. However, regarding the setting of the aspect ratio, an operation of the aspect ratio setting part 325 can be immediately reflected in display.

The sectional position display switching part 327 is used for switching on/off the display of an image indicating the position of the cross section of a cross-sectional image (slice position). Such an image is displayed over at least one of a C cross-sectional image, a B cross-sectional image and a front image. An image indicating the cross section position of the B cross-sectional image is displayed over the C cross-sectional image. An image indicating the cross section position of the C cross-sectional image is displayed over the B cross-sectional image. An image indicating the cross section position of the B cross-sectional image is also displayed over the front image. Note that an image indicating a scanning area of three-dimensional scan, that is, an image indicating an area corresponding to three-dimensional image data (a rectangular (square) image, for example) is displayed over the front image.

The layer position display switching part 328 is used for switching on/off the display of line images indicating the positions of layer tissues and/or layer boundaries represented in the B cross-sectional image. The positions of layer tissues and/or layer boundaries are obtained by executing known image analysis to the B cross-sectional image.

The grayscale inverting part 329 is operated for inverting gradation values of the C cross-sectional image displayed as a grayscale image.

Further, the window 300 shown in FIG. 4A is provided with a processed image selecting part 331, a projection range setting parts 332a and 332b, and a processed image export instructing part 333. The processed image selecting part 331, the projection range setting parts 332a and 332b, and the processed image export instructing part 333 are used for operations regarding processed images. The processed image selecting part 331 is a drop-down list, for example, and a list of kinds of processed images is presented in the drop-down list. The user selects a desired kind of a processed image using the operation part 242. When shadowgram is selected, the user selects desired layer tissues from lists presented in the projection range setting parts 332a and 332b wherein the lists are drop-down lists. A projection range indicates data included an area between two layer tissues set by means of the projection range setting parts 332a and 332b. The image processor 230 forms processed image data of the selected kind based on the three-dimensional image data. The main controller 211 displays a processed image based on the processed image data on processed image display part 305. The processed image export instructing part 333 is operated for exporting the processed image data.

Further, the window 300 shown in FIG. 4A is provided with a front image selecting part 341, a front image importing part 342, and an enhancement instructing part 343. The front image selecting part 341, the, and the enhancement instructing part 343 are used for operations regarding front images. The front image selecting part 341 is a drop-down list, for example, and a list of front images that can be displayed in the front image display part 304. The front image importing part 342 is operated for importing front image data. When the front image importing part 342 is clicked, a predetermined dialogue is displayed as a pop-up. A list of importable front image data is presented in the dialogue. When the user selects front image data, processing shifts to position matching between the selected front image data and image data already imported (three-dimensional image data, front image data, and the like). The position matching is performed automatically, semi-automatically, or manually. In automatic position matching, for example, the image processor 230 analyzes each of two image data to extract predetermined feature points (three feature points, for example), and performs affine transformation between the two image data such that the respective feature points coincide with each other. In semi-automatic position matching, for example, the main controller 211 displays two images based on two image data side by side. The user designates the abovementioned feature points using the operation part 242. The image processor 230 performs affine transformation between the two image data such that the respective feature points coincide with each other. In manual position matching, the user adjusts the sizes, orientations and positions of two images using operation part 242. The enhancement instructing part 343 is operated for applying enhancement processing to a front image displayed in the front image display part 304.

Further, the window 300 shown in FIG. 4A is provided with a setting button 351, an export button 352 and a screen shot button 353. When the setting button 351 is clicked, a setting screen (not illustrated) is displayed. The user performs settings of an export destination, a storage location of a screen shot, the pixel size of an image, a format of image data, and the like by means of the setting screen. The export button 352 is used for designating a folder to be an export destination. The screen shot button 353 is used for designating a folder to be a storage location of a screen shot (a hard copy).

(Display of Images)

The user selects three-dimensional image data by means of the data selecting part 312 and selects front image data by means of the front image selecting part 341. Base on the three-dimensional image data, the main controller 211 displays a C cross-sectional image in a default C cross section on the transverse cross-sectional image display part 301, and displays two B cross-sectional images 402 and 403 in two default B cross sections orthogonal to each other on the longitudinal cross-sectional image display parts 302 and 303, respectively (see FIG. 4B). These cross-sectional images (cross-sectional image data) are based on the three-dimensional image data before deformation, and correspond to the aforementioned "standard cross-sectional image (cross-sectional image data)".

Here, the default C cross section and the two default B cross sections are arbitrary set. For example, the default C cross section corresponds to the center position of the frame of the B cross-sectional image 402 (and the B cross-sectional image 403) in the z-direction, and the two default B cross section corresponds to the center position in the x-direction and the center position in the y-direction of the frame of the C cross-sectional image 401. Here, the x-direction corresponds to the horizontal direction of the window 300, and the y-direction corresponds to the vertical direction. Therefore, the B cross-sectional image 402 passes through the center position in the horizontal direction of the frame of the C cross-sectional image 401, and represents a cross section along a scanning line extending in the vertical direction of the window 300; and the B cross-sectional image 403 passes through the center position in the vertical direction of the frame of the C cross-sectional image 401, and represents a cross section along a scanning line extending in the horizontal direction of the window 300

Further, the main controller 211 displays a B cross section position image (a straight line image 502 shown by a broken line) indicating the sectional position of the B cross-sectional image 402 and a B cross section position image (a straight line image 501 shown by a broken line) indicating the sectional position of the B cross-sectional image 403 over the C cross-sectional image 401. The main controller 211 displays C cross section position images (straight line images 511 and 512 shown by broken lines) indicating the sectional positions of the C cross-sectional image 401 over the B cross-sectional images 402 and 403, respectively. Note that the straight line image 501 extends to the B cross-sectional image 402, thereby indicating the sectional position of the B cross-sectional image 403 in the B cross-sectional image 402. Similarly, the straight line image 502 extends to the B cross-sectional image 403, thereby indicating the sectional position of the B cross-sectional image 402 in the B cross-sectional image 403. The straight line images 501 and 502 are examples of a "longitudinal section position image" and the straight line images 511 and 512 are examples of a "transverse section position image".

The main controller 211 displays a front image 404 based on the front image on the front image display part 304. Further, the main controller 211 displays a rectangular image 521 indicating the area of three-dimensional scan, a sectional position image (straight line image) 522 indicating the sectional position of the B cross-sectional image 402, and a sectional position image (straight line image) 523 indicating the sectional position of the B cross-sectional image 403 over the front image 404. The sectional position images 522 and 523 are examples of the "longitudinal section position image".

The user can switch display/non-display of the straight line images 501, 502, 511, 512, 522 and 523 by operating the sectional position display switching part 327.

(Deformation of Three-dimensional Image Data)

The deformation of three-dimensional image data is described. The user clicks the deformation execution instructing part 321. Subsequently, the user selects a desired item (specific site) from the list of layer tissues and layer boundaries presented in the standard layer selecting part 322. It is assumed that Bruch membrane (BM) is selected here. Further, the user sets a range (the number of pixels) of averaging for formation of a C cross-sectional image using the averaging range setting part 324. Next, the user instructs the apparatus 1 to execute processing based on the above setting contents by clicking the update button 326.

When the instruction of execution of deformation of the three-dimensional image data is performed, the partial image data designating part 232 analyzes the B cross-sectional image 402 (or the B cross-sectional image 403) on display to specify an image area corresponding to the selected specific site (Bruch membrane). This processing is performed based on the pixel values (brightness values) of the B cross-sectional image 402. This processing may include known processing such as curve fitting. Further, based on the ixel values (brightness values) of the three-dimensional image data, the partial image data designating part 232 expands the image area specified in the B cross-sectional image 402 to a data area corresponding to the specific site in the totality of the three-dimensional image data. The processing may include image correlation to data of adjacent B cross section. An area in the three-dimensional image data specified by this processing is used as the aforementioned "partial image data".

Figure 4B:
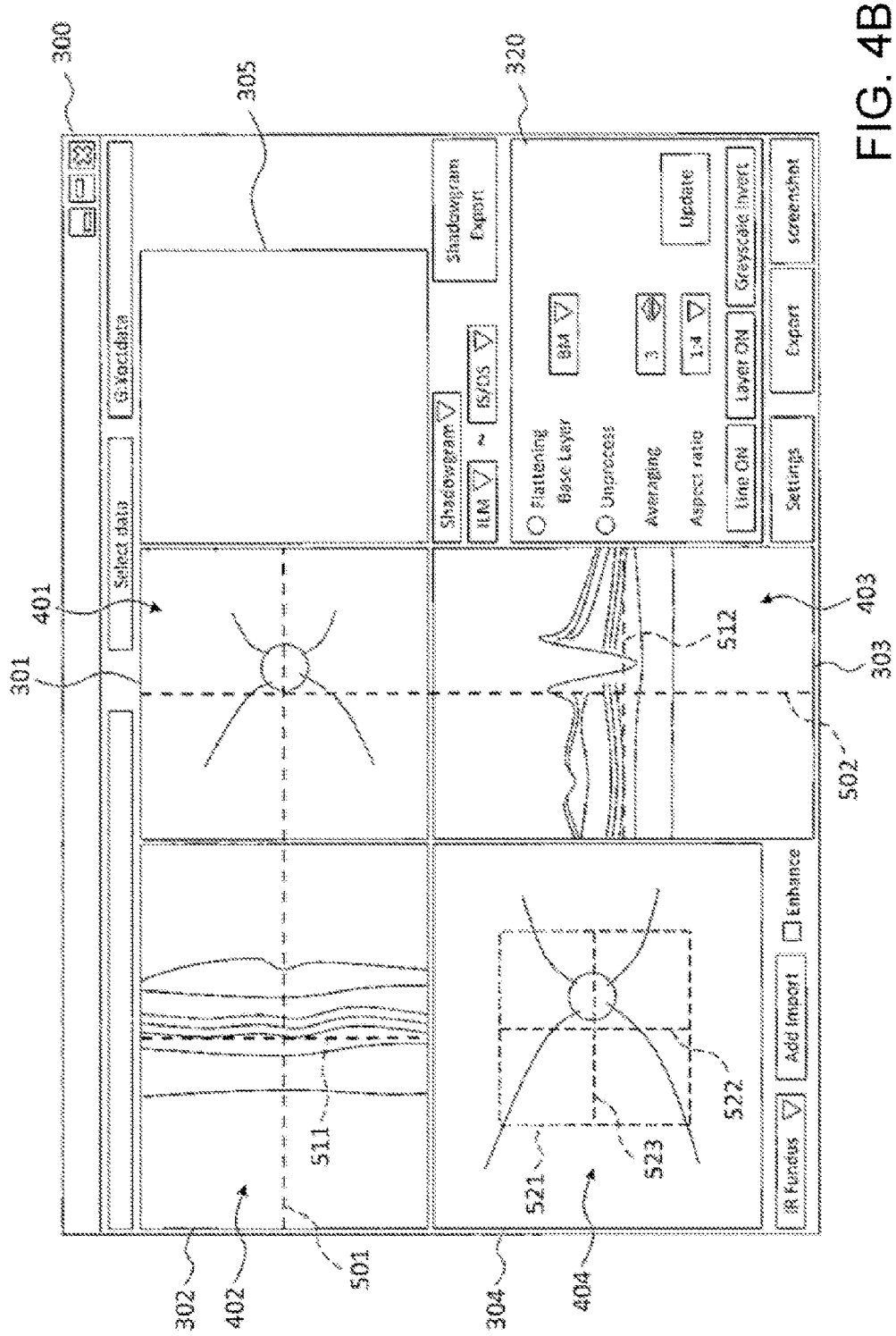
FIG. 4B is a schematic diagram for illustrating an operation example of an ophthalmologic imaging apparatus according to an embodiment.
Figure 4C:
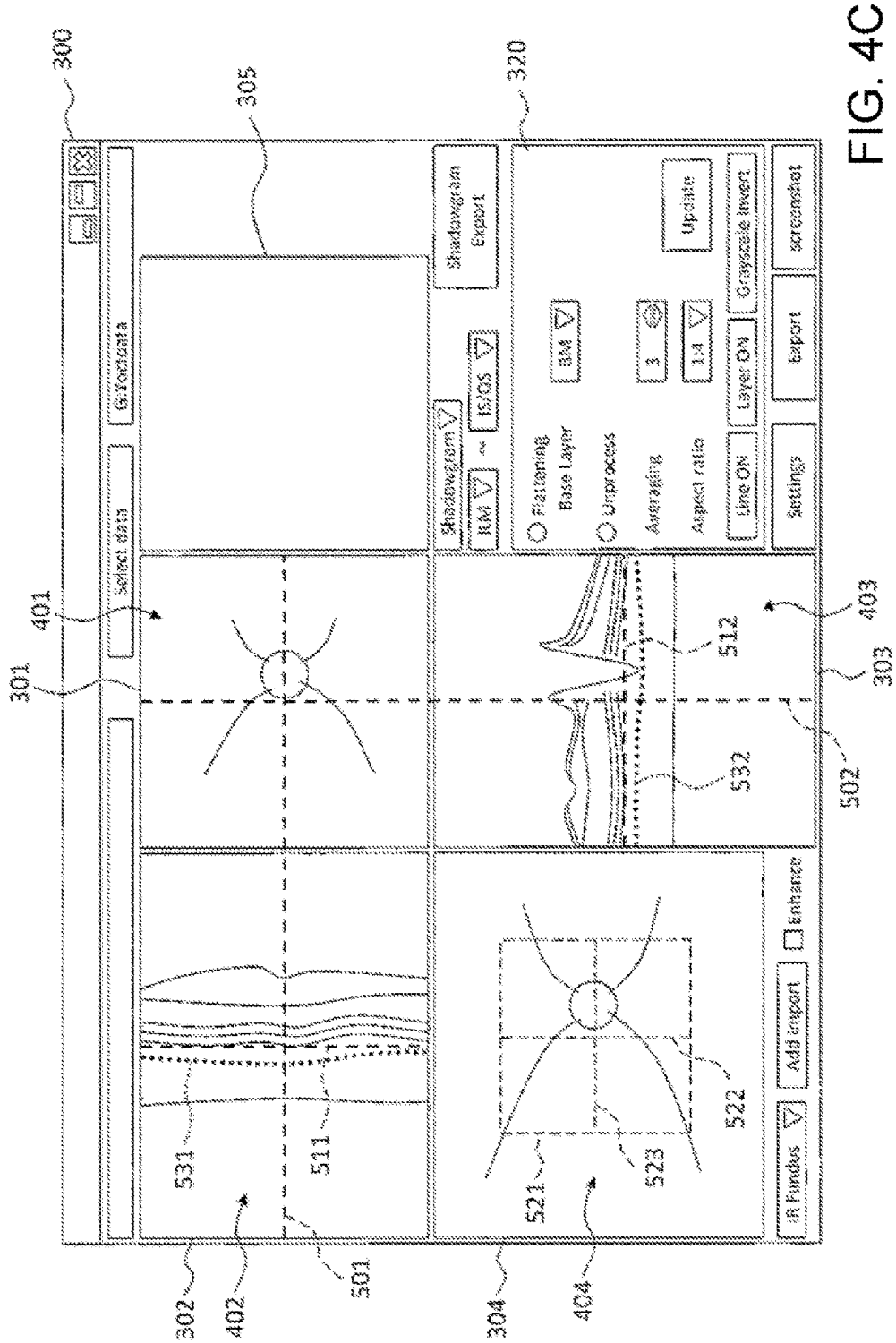
FIG. 4C is a schematic diagram for illustrating an operation example of an ophthalmologic imaging apparatus according to an embodiment.

The main controller 211 changes the display aspect of the areas in the B cross-sectional images 402 and 403 corresponding to the selected specific site (Bruch membrane). A display state at the time of execution of this processing is shown in FIG. 4C. In FIG. 4C, a curved line image 531 shown by a dotted line on the B cross-sectional images 402 and a curved line image 532 shown by a dotted line on the B cross-sectional images 403 indicate the selected specific site (Bruch membrane).

Next, the image data deforming part 233 performs deformation of the three-dimensional image data such that the partial image data (two-dimensional area) designated by the partial image data designating part 232 is deformed into a planar shape. The cross-sectional image data forming part 234 forms applies MPR processing or the like to the deformed three-dimensional image data to form new C cross-sectional image data and two new B cross-sectional image data orthogonal to each other. The cross sections of these cross-sectional image data are the same as those of the C cross-sectional image 401, the B cross-sectional images 402 and 403 displayed in the window 300 immediately before the image data formation, for example. The new C cross-sectional image data is formed by averaging C cross-sectional image data included in the averaging area (the number of pixels) set by means of averaging range setting part 324.

The main controller 211 displays, instead of the C cross-sectional image 401, a new C cross-sectional image based on the new C cross-sectional image data in the transverse cross-sectional image display part 301. Further, the main controller 211 displays, instead of the B cross-sectional images 402 and 403, two new B cross-sectional images based on the two new B cross-sectional image data in the longitudinal cross-sectional image display parts 302 and 303.

Figure 4D:
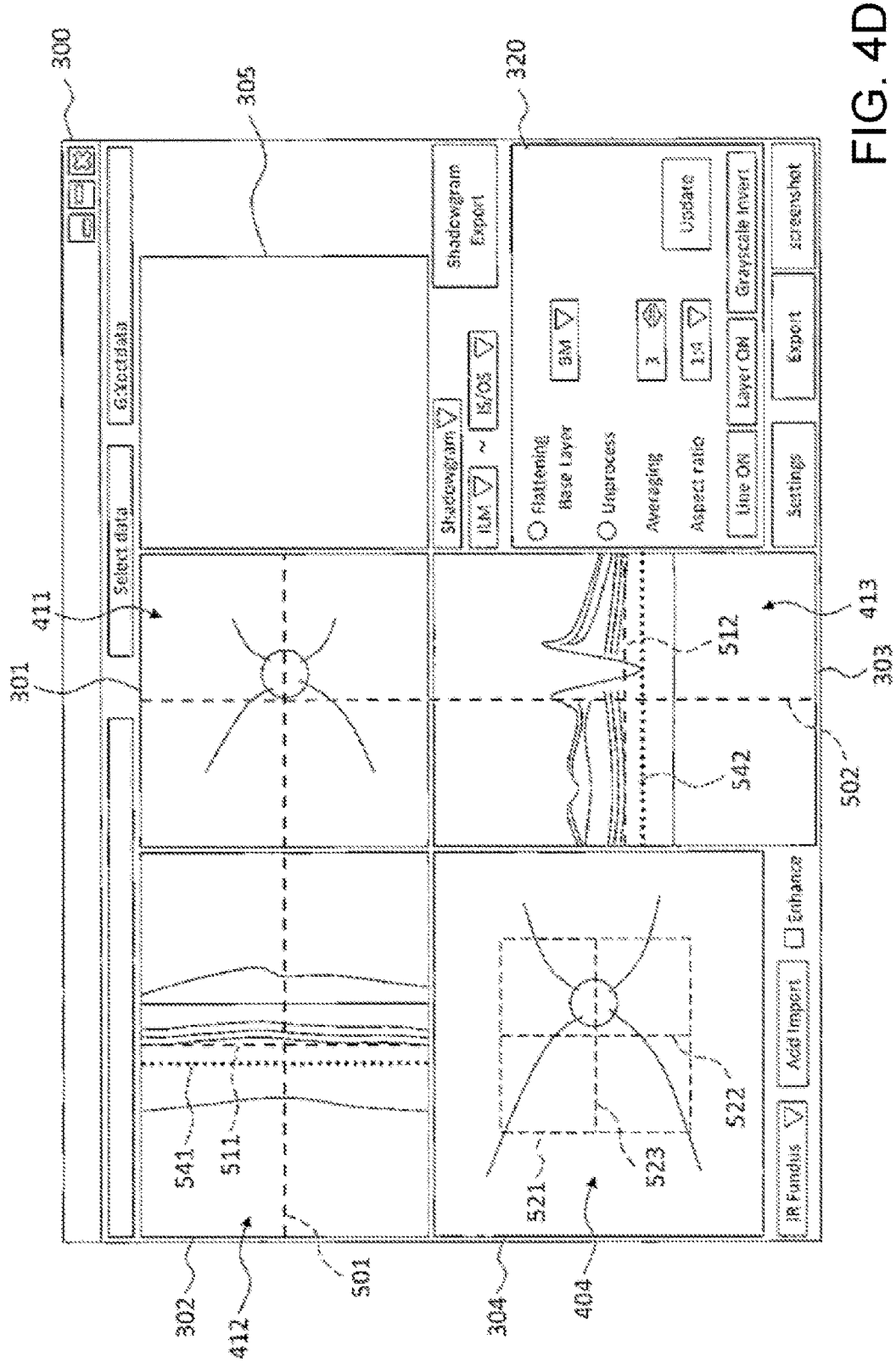
FIG. 4D is a schematic diagram for illustrating an operation example of an ophthalmologic imaging apparatus according to an embodiment.

In the new C cross-sectional image and the new B cross-sectional images, the specific site (Bruch membrane) is presented in a straight line shape. An example of such cross-sectional images is shown in FIG. 4D. FIG. 4D illustrates a new C cross-sectional image 411 and new B cross-sectional images 412 and 413.

In the new B cross-sectional image 412, the specific site (Bruch membrane) presented by the curved line image 531 before deformation is now presented as a straight line image 541. Further, other areas in the new B cross-sectional image 412 are represented with deformation in accordance with the deformation from the curved line image 531 to the straight line image 541. The straight line image 541 is represented in a display aspect different from those of other areas, for example.

Similarly, the new B cross-sectional images 413, the specific site (Bruch membrane) presented by the curved line image 532 before deformation is now presented as a straight line image 542. Further, other areas in the new B cross-sectional images 413 are represented with deformation in accordance with the deformation from the curved line image 532 to the straight line image 542. The straight line image 542 is represented in a display aspect different from those of other areas, for example.

In this way, the user can observe a B cross-sectional image in which a desired site of the eye E is flattened. According to such a B cross-sectional image, positional relationship between the desired site and other sites is easily understood. By setting a C cross section at the desired site for the change in a C cross section position described below, a C cross-sectional image representing the morphology of the desired site (Bruch membrane or the like) can be observed.

(Change in C Cross Section Position)

Processing of changing a C cross section position is described. A C cross section is a section parallel to the xy-plane that is orthogonal to the z-direction. The cross section position of the C cross-sectional image 411 displayed in the transverse cross-sectional image display part 301 is indicated by the straight line image 511 (C cross section position image) on the B cross-sectional image 412 and the straight line image 512 (C cross section position image) on the B cross-sectional images 413.

The straight line image 511 is movable in the z-direction (the horizontal direction in the longitudinal cross-sectional image display part 302). Similarly, the straight line image 512 is movable in the z-direction (the vertical direction in the longitudinal cross-sectional image display parts 303). The user can move the straight line image 511 or 512 in the z-direction using the operation part 242 (pointing device such as a mouse, for example).

When the straight line image 511 (or 512) is moved, the main controller 211 sends positional information (z coordinate value) of the straight line image 511 (or 512) after the movement to the cross-sectional image data forming part 234. The cross-sectional image data forming part 234 applies MPR processing or the like to the deformed three-dimensional image data to form C cross-sectional image data in a C cross section at the z coordinate value. The C cross-sectional image data is sent to the main controller 211. The main controller 211 displays, instead of the C cross-sectional image displayed until just before, a new C cross-sectional image based on the C cross-sectional image data on the transverse cross-sectional image display part 301.

There are cases in which the straight line image 511 (or 512) is continuously moved. In such cases, the main controller 211 sends position information of the straight line image 511 (or 512) being continuously moved one after another to the cross-sectional image data forming part 234. The cross-sectional image data forming part 234 successively forms C cross-sectional image data based on position information input one after another. The successively formed C cross-sectional image data is successively sent to the main controller 211. The main controller 211 updates an image displayed in the transverse cross-sectional image display part 301 with new C cross-sectional images based on C cross-sectional image data input successively.

In this way, the user can observe the morphology of a desired C cross section.

(Change in B Cross Section Position)

Processing of changing a B cross section position is described. A B cross section is a section along the z-direction. In the present embodiment, the B cross-sectional image 412 in the yz cross section and the B cross-sectional image 413 in the xz cross section are displayed. The cross section position of the B cross-sectional image 412 displayed in the longitudinal cross-sectional image display part 302 is indicated by the straight line image 502 (B cross section position image) presented on the C cross-sectional image 411 and the B cross-sectional image 413. Similarly, the cross section position of the B cross-sectional image 413 displayed in the longitudinal cross-sectional image display part 303 is indicated by the straight line image 501 (B cross section position image) presented on the C cross-sectional image 411 and the B cross-sectional image 412. Further, the straight line images 522 and 523 presented on the front image 404 indicate the cross section positions of the B cross-sectional images 412 and 413, respectively.

The straight line image 501 is movable in the y-direction (the vertical direction in the transverse cross-sectional image display parts 301). Similarly, the straight line image 502 is movable in the x-direction (the horizontal direction in the transverse cross-sectional image display parts 301). The user can move the straight line image 501 and 502 using the operation part 242 (pointing device such as a mouse, for example).

When the straight line image 501 (or 502) is moved, the main controller 211 sends positional information of the straight line image 501 (or 502) after the movement to the cross-sectional image data forming part 234. The cross-sectional image data forming part 234 applies MPR processing or the like to the deformed three-dimensional image data to form B cross-sectional image data in a B cross section indicated by the position information. The B cross-sectional image data is sent to the main controller 211. The main controller 211 displays, instead of the B cross-sectional image displayed until just before, a new B cross-sectional image based on the B cross-sectional image data on the longitudinal cross-sectional image display part 303 (or 302).

There are cases in which the straight line image 501 (or 502) is continuously moved. In such cases, the main controller 211 sends position information of the straight line image 501 (or 502) being continuously moved one after another to the cross-sectional image data forming part 234. The cross-sectional image data forming part 234 successively forms B cross-sectional image data based on position information input one after another. The successively formed B cross-sectional image data is successively sent to the main controller 211. The main controller 211 updates an image displayed in the longitudinal cross-sectional image display part 303 (or 302) with new B cross-sectional images based on B cross-sectional image data input successively.

In this way, the user can observe the morphology of a desired B cross section.

[Effects]

Effects of the ophthalmologic imaging apparatus 1 are described.

The ophthalmologic imaging apparatus 1 includes an acquiring part, a designating part, a deforming part, a forming part, and a display controller.

The acquiring part includes the OCT unit 100, elements of the retinal camera unit 2 that form the optical path of the signal light LS, the image forming part 220, and the three-dimensional image data forming part 231. The acquiring part acquires three-dimensional image data of the eye E by using optical coherence tomography.

The designating part includes the partial image data designating part 232. The designating part may include the user interface 240. The designating part functions so as to designate partial image data that is a part of the three-dimensional image data corresponding to a specific site of the eye E.

The deforming part includes the image data deforming part 233. The deforming part deforms the three-dimensional image data such that the partial image data designated by the designating part is deformed into a predetermined shape, thereby creating new three-dimensional image data.

The forming part includes the cross-sectional image data forming part 234. The forming part forms cross-sectional image data based on the new three-dimensional image data created by the deforming part.

The display controller includes the main controller 211. The display controller displays an image based on the cross-sectional image data formed by the forming part on a display means. The display means may be included in the ophthalmologic imaging apparatus 1 as in the present embodiment (the display 241), or may be provided outside the ophthalmologic imaging apparatus 1.

According to the ophthalmologic imaging apparatus 1 thus configured, a cross-sectional image can be displayed in which the specific site of the eye E is represented in the predetermined shape. Accordingly, while paying attention to the specific site during observation, relations between the specific site and other sites can be easily comprehended. For example, while paying attention to a specific layer of a retina (Bruch membrane or the like), the user can easily comprehend the shape of another layer with the specific layer as a standard, the distance between the specific layer and another layer, and the like. In this manner, the ophthalmologic imaging apparatus 1 of the present embodiment is capable of providing a new technique of ophthalmologic diagnostic imaging.

In embodiments, the partial image data corresponding to the specific site of the eye E may be a two-dimensional area in the three-dimensional image data. If this is the case, the deforming part is capable of performing deformation of the three-dimensional image data such that the two-dimensional area is deformed into a planar shape or a predetermined curved shape.

With this configuration, it is possible to suitably observe an arbitrary tissue (a layer tissue, a layer boundary, and the like) that can substantially be thought as a two-dimensional area of the eye E. Here, a shape of the two-dimensional area after deformation can be set arbitrarily according to the morphology of the specific site, the object of observation.

There are cases in which partial image data is not a two-dimensional area. For example, when partial image data is a three-dimensional area, three-dimensional image data is deformed such that the three-dimensional area is deformed into an arbitrary shape. The shape after deformation can be a rectangle, a square, a predetermined curved plate, or the like.

In embodiments, the forming part forms, as the cross-sectional image data, transverse cross-sectional image data (C cross-sectional image data) in a transverse section (xy-plane) that is substantially orthogonal to a traveling direction (z-direction) of light (signal light LS) irradiated to the eye E in optical coherence tomography. Further, the display controller displays, on the display means, a transverse cross-sectional image (C cross-sectional image) based on the transverse cross-sectional image data.

With such a configuration, a cross-sectional image in the transverse direction (xy-direction) can be observed. In particular, the morphology of the specific site deformed into a planar shape can be observed as a transverse cross-sectional image. Like layer tissues and layer boundaries of the fundus Ef, some tissues of the eye E are extended in the xy-direction and have shapes bent or curved in the z-direction. With conventional imaging technology, since not only the targeted tissue but also other tissues are represented in a transverse cross-sectional image, it is impossible to observe only the targeted tissue. In contrast, the embodiment enables the user to observe a transverse cross-sectional image representing the targeted tissue only, thereby observing the state of this tissue in detail.

In embodiments, a first operation part for designating a position of the transverse section (xy-plane) can be provided. The first operation part includes the user interface 240. In the above embodiment, the first operation part includes the straight line images 511 and 512 and the operation part 242. The forming part forms new transverse cross-sectional image data in a transverse section designated using the first operation part. The display controller updates a transverse cross-sectional image displayed on the display means based on the new transverse cross-sectional image data. The update processing is replacement of transverse cross-sectional images displayed.

With such a configuration, the user can observe a desired transverse section in the area of the eye E for which three-dimensional image data is acquired (that is, the scanning area to which three-dimensional scan is performed).

In embodiments, the forming part is capable of forming, as the cross-sectional image data, longitudinal cross-sectional image data (B cross-sectional image data) in a longitudinal section (B cross section) orthogonal to the transverse section (C cross section). Further, the display controller is capable of performing the following display processing: (1) the display controller arranges and displays a longitudinal cross-sectional image (B cross-sectional image) based on the longitudinal cross-sectional image data and the transverse cross-sectional image (C cross-sectional image); (2) the display controller displays a longitudinal section position image (straight line images 501 and 502, for example) indicating a sectional position (C cross section position) of the longitudinal cross-sectional image together with the transverse cross-sectional image; and (3) the display controller displays a transverse section position image (straight line images 511 and 512, for example) indicating a sectional position of the transverse cross-sectional image together with the longitudinal cross-sectional image.

With such a configuration, both transverse and longitudinal cross-sectional images of the eye E can be observed and positional relationship between the transverse and longitudinal cross-sectional images can be comprehended easily. Therefore, suitable diagnosis support can be realized.

In embodiments, the forming part is capable of forming, as the longitudinal cross-sectional image data, first longitudinal cross-sectional image data and second longitudinal cross-sectional image data in two longitudinal sections orthogonal to each other. Further, the display controller is capable of performing the following display processing: (1) the display controller arranges and displays a first longitudinal cross-sectional image (B cross-sectional image 402 or 412, for example) based on the first longitudinal cross-sectional image data, a second longitudinal cross-sectional image (B cross-sectional image 403 or 413, for example) based on the second longitudinal cross-sectional image data and the transverse cross-sectional image (C cross-sectional image 401 or 411, for example); (2) the display controller displays a first longitudinal section position image (straight line image 502, for example) indicating a sectional position of the first longitudinal cross-sectional image and a second longitudinal section position image (straight line image 501, for example) indicating a sectional position of the second longitudinal cross-sectional image together with the transverse cross-sectional image; and (3) the display controller displays the transverse section position image (straight line images 511 and 512, for example) indicating a sectional position of the transverse cross-sectional image together with each of the first and second longitudinal cross-sectional images. Here, it is also possible to display the first longitudinal section position image (straight line image 502, for example) indicating the sectional position of the first longitudinal cross-sectional image together with the second longitudinal cross-sectional image, and the second longitudinal section position image (straight line image 501, for example) indicating the sectional position of the second longitudinal cross-sectional image together with the first longitudinal cross-sectional image.

With such a configuration, a transverse cross-sectional image and two mutually orthogonal longitudinal cross-sectional images of the eye E can be observed, and positional relationship between the transverse cross-sectional image and the respective longitudinal cross-sectional images (and also positional relationship between the two longitudinal cross-sectional images) can be comprehended easily. Therefore, suitable diagnosis support can be realized.

In embodiments, a second operation part for designating a position of the longitudinal section (B cross section) may be provided. The second operation part includes the user interface 240. In the above configuration, the second operation part includes the straight line images 501 and 502 and the operation part 242. The forming part forms new longitudinal cross-sectional image data in a longitudinal section designated using the second operation part. The display controller is capable of performing the following processing: (1) the display controller updates a longitudinal cross-sectional image displayed on the display means based on the new longitudinal cross-sectional image data; and (2) the display controller changes a display position of the longitudinal section position image (straight line images 501 and 502, for example) with respect to the transverse cross-sectional image (C cross-sectional image 401 or 411, for example) based on the longitudinal section (B cross section) designated using the second operation part.

With such a configuration, the user can observe a desired longitudinal section in the area of the eye E for which three-dimensional image data is acquired (that is, the scanning area to which three-dimensional scan is performed).

In embodiments, a photographing part that photographs the eye E to obtain front image data may be provided. Further, the display controller is capable of performing the following processing: (1) the display controller arranges and displays a front image (front image 404, for example) based on the front image data, the transverse cross-sectional image and the longitudinal cross-sectional image; and (2) the display controller displays the longitudinal section position image (straight line images 522 and 523, for example) together with the front image.

With such a configuration, the user can easily understand the location, in the front image, of the cross section of the longitudinal cross-sectional image on display. Here, the position matching between the front image data and the three-dimensional image data can be performed by forming a processed front image (shadowgram or the like) based on the three-dimensional image data and performing position matching between the processed front image and the front image.

In embodiments, a third operation part may be provided. The third operation part includes the user interface 240. In the above configuration, the third operation part includes the display 241 (screens displayed in the window 300) and the operation part 242. The forming part forms standard cross-sectional image data in a standard section (arbitrary B cross section) substantially along a traveling direction (z-direction) of light (signal light LS) irradiated to the eye E in optical coherence tomography based on the three-dimensional image data acquired by the acquiring part. The display controller displays a standard cross-sectional image (B cross-sectional images 402 and 403, for example) based on the standard cross-sectional image data on the display means. When an image area in the standard cross-sectional image is designated using the third operation part, the designating part is capable of analyzing the three-dimensional image data based on the designated image area to perform designation of the partial image data. The image area designated by the third operation part corresponds to the specific site of the eye E.

With such a configuration, the user can observe the standard cross-sectional image and comprehend a site of interest, and also, can observe an image in which the site of interest is deformed in to a predetermined shape.

In embodiments, a fourth operation part may be provided. The fourth operation part includes the user interface 240. In the above configuration, the fourth operation part includes the display 241 (screens displayed in the window 300) and the operation part 242. The display controller is capable of displaying, on the display means, selection information (standard layer selecting part 322, for example) in which a plurality of tissues of an eye is selectably presented. When a tissue (Bruch membrane, for example) of the plurality of tissues presented in the selection information is selected using the fourth operation part, the designating part is capable of analyzing the three-dimensional image data based on the selected tissue to specify a part of the three-dimensional image data corresponding to the selected tissue. The part specified is used as the partial image data.

With such a configuration, the user can select a desired tissue from among choices presented in the selection information, and can observe an image in which the selected tissue is deformed into a predetermined shape.

In embodiments, the forming part forms standard cross-sectional image data in a standard section (arbitrary B cross section) substantially along a traveling direction (z-direction) of light (signal light LS) irradiated to the eye E in optical coherence tomography based on the three-dimensional image data acquired by the acquiring part. The display controller is capable of performing the following display processing: (1) the display controller displays a standard cross-sectional image (B cross-sectional images 402 and 403, for example) based on the standard cross-sectional image data on the display means; and (2) when a tissue (Bruch membrane, for example) of the plurality of tissues is selected using the fourth operation part, the display controller changes a display aspect of a part of the standard cross-sectional image corresponding to the selected tissue (curved line images 531 and 532, for example).

With such a configuration, it is possible to clearly indicate, in the standard cross-sectional image, the tissue selected from the selection information by the user. Incidentally, the change in the display aspect can be reflected to a cross-sectional image displayed after the update.

[First Modification]

In the above embodiments, the optical path length difference between the optical path of the signal light LS and the optical path of the reference light LR is changed by changing the position of the optical-path-length changing part 41; however the method of changing the optical path length difference is not limited to this. For example, the optical path length difference can be changed by providing a reflection mirror (reference mirror) in the optical path of reference light and moving the reference mirror in the traveling direction of the reference light to change the optical path length of the reference light. Alternatively, the optical path length difference can be changed by moving the retinal camera unit 2 and/or the OCT unit 100 relative to the eye E to change the optical path length of the signal light LS.

One of a front image and a transverse cross-sectional image of the eye E can be overlaid with the other. For example, a transverse cross-sectional image can be displayed over a front image. Besides the acquiring part, the designating part, the deforming part, the forming part and the display controller, an ophthalmologic imaging apparatus according to the present modification includes a photographing part that photographs the eye E to obtain front image data. The front image data is, for example, image data acquired by any photographing unit such as the retinal camera unit, an SLO unit, a slit lamp unit, or the like. Examples thereof include color fundus image data, fluorescein angiography image data, indocyanine green fluorescent image data, autofluorescent image data, infrared image data, and the like. Further, the display controller displays a front image based on the front image data and a transverse cross-sectional image (C cross-sectional image data) based on transverse cross-sectional image data overlapped with each other.

In such processing, position matching between the front image data and the transverse cross-sectional image data (or volume data) can be performed. The position matching is registration between front image data based on the volume data and front image data acquired by the photographing part, for example. The front image data based on the volume data is the transverse cross-sectional image data to be displayed itself or a shadowgram, for example. The shadowgram is created by adding an area including at least data corresponding to the surface of the fundus and the vicinity thereof. The position matching between these front image data includes, for example, image correlation, position matching of feature points, or the like. According to such processing, when the position of a transverse section is changed, a transverse cross-sectional image at the position of the changed transverse section can be displayed over the front image.

Although the ophthalmologic imaging apparatus of the present modification includes the photographing part, a configuration can be employed that receives front image data acquired by another ophthalmologic imaging apparatus, and displays a front image based on the received front image data and a transverse cross-sectional image based on transverse cross-sectional image data formed from volume data acquired by itself overlapped with each other.

A volume rendering image, instead of a transverse cross-sectional image, and a front image can be overlaid with each other. More specifically, display control can be performed such that an area corresponding to the retinal surface in pseudo three-dimensional image data formed by volume rendering and a front image are overlapped with each other. Position matching in this processing is performed in the same way as above.

[Second Modification]

The image processor 230 may include an analyzer that analyzes volume data. The analyzer is capable of obtaining the distance (thickness) between a first layer tissue (layer boundary) and a second layer tissue (layer boundary) of the fundus Ef, for example. This processing includes the following steps, for example: (1) specifying a first voxel corresponding to the first layer tissue and a second voxel corresponding to the second layer tissue of the voxels on each A-line of the volume data; (2) calculating the distance between the first voxel and the second voxel for each A-line. With such processing, the distances between the first layer tissue and the second layer tissue (interlayer distance) for the respective A-lines of the volume data is obtained. This represents distribution of interlayer distances of a defined range in the xy-coordinate system of the volume data.

The display controller is capable of presenting the distribution information as visual information. Examples of display aspects thereof include thickness map display, graph display, and the like. The thickness map display is color map display, for example. The color map display is performed by dividing the range of values interlayer distances in the distribution information into a plurality of subranges, assigning display colors to the respective subranges, and setting pixel values of the respective pixels (xy-coordinate values) according to this assignment. The display controller is capable of displaying a display image such as the color map together with one or more of a transverse cross-sectional image, a longitudinal cross-sectional image and a front image. A display aspect thereof is side-by-side display or overlay display. The side-by-side display is a method of arranging and displaying distribution image and one or more of a transverse cross-sectional image, a longitudinal cross-sectional image and a front image. The overlay display is a method of superposing and displaying distribution image and a transverse cross-sectional image and/or a front image.

[Third Modification]

Although the above embodiment describes observation of the morphology of a C cross section orthogonal to the z-direction or a B cross section along the z-direction, a configuration may be employed so as to observe the morphology of a cross section orthogonal to an arbitrary direction. In the present modification, the partial image data designating part 232 designates partial image data corresponding to a specific site in three-dimensional image data of the eye by means of manual setting or automatic setting in the same way as in the above embodiment. A direction of a cross section can be arbitrarily designated to the designated partial image data manually or automatically.

(Manual Designation of Direction of Cross Section)

Figure 5:
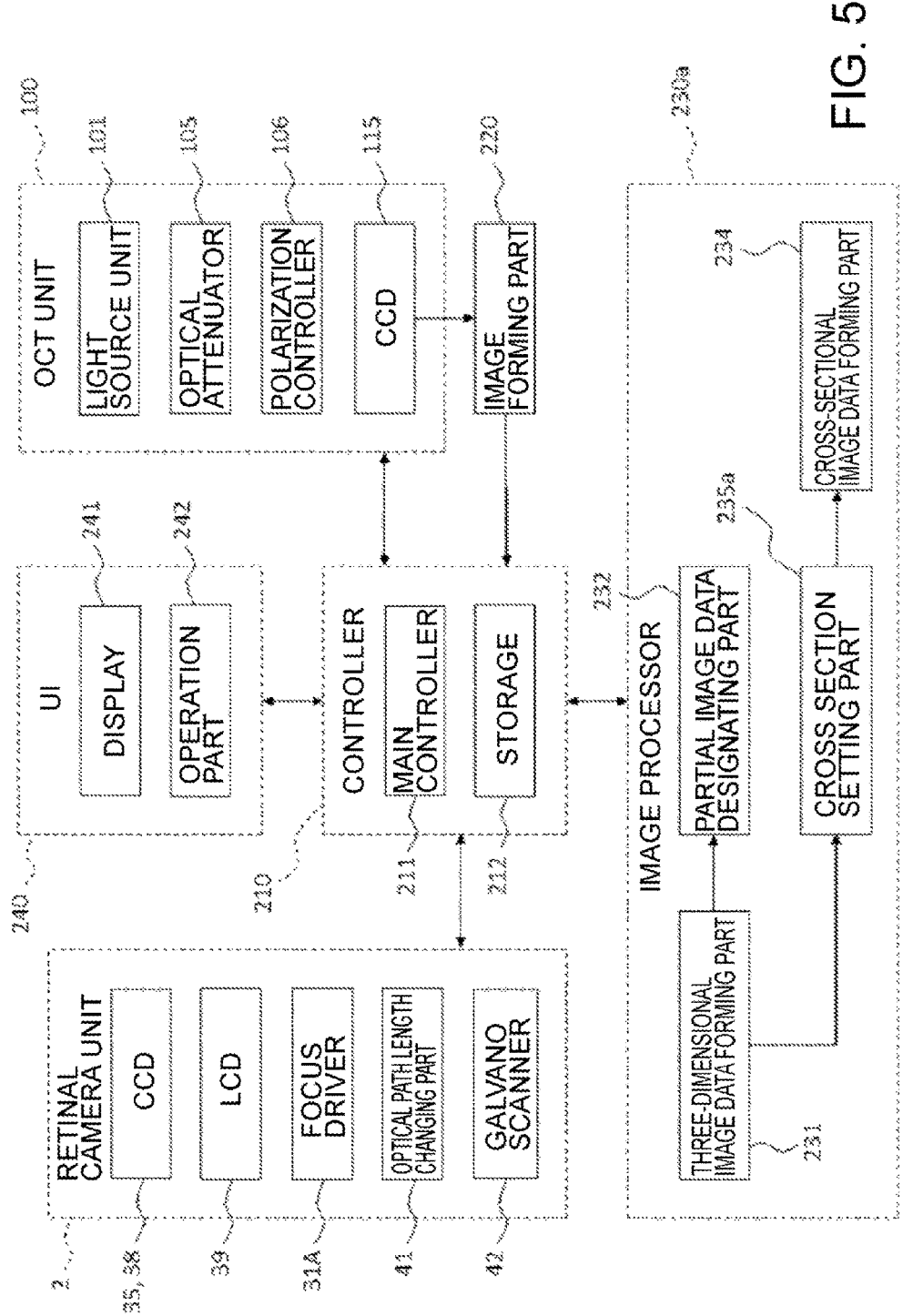
FIG. 5 is a schematic block diagram illustrating a configuration example of a third modification of an embodiment.

FIG. 5 illustrates a configuration of the control system of an ophthalmologic imaging apparatus according to a third modification of the embodiment. FIG. 5 illustrates a configuration example of the control system applicable to a case of designating a direction of a cross section to a partial image data by hand. In FIG. 5, the same numeral symbols are assigned to like parts in FIG. 3, and description thereof are omitted unless required.

Figure 3:
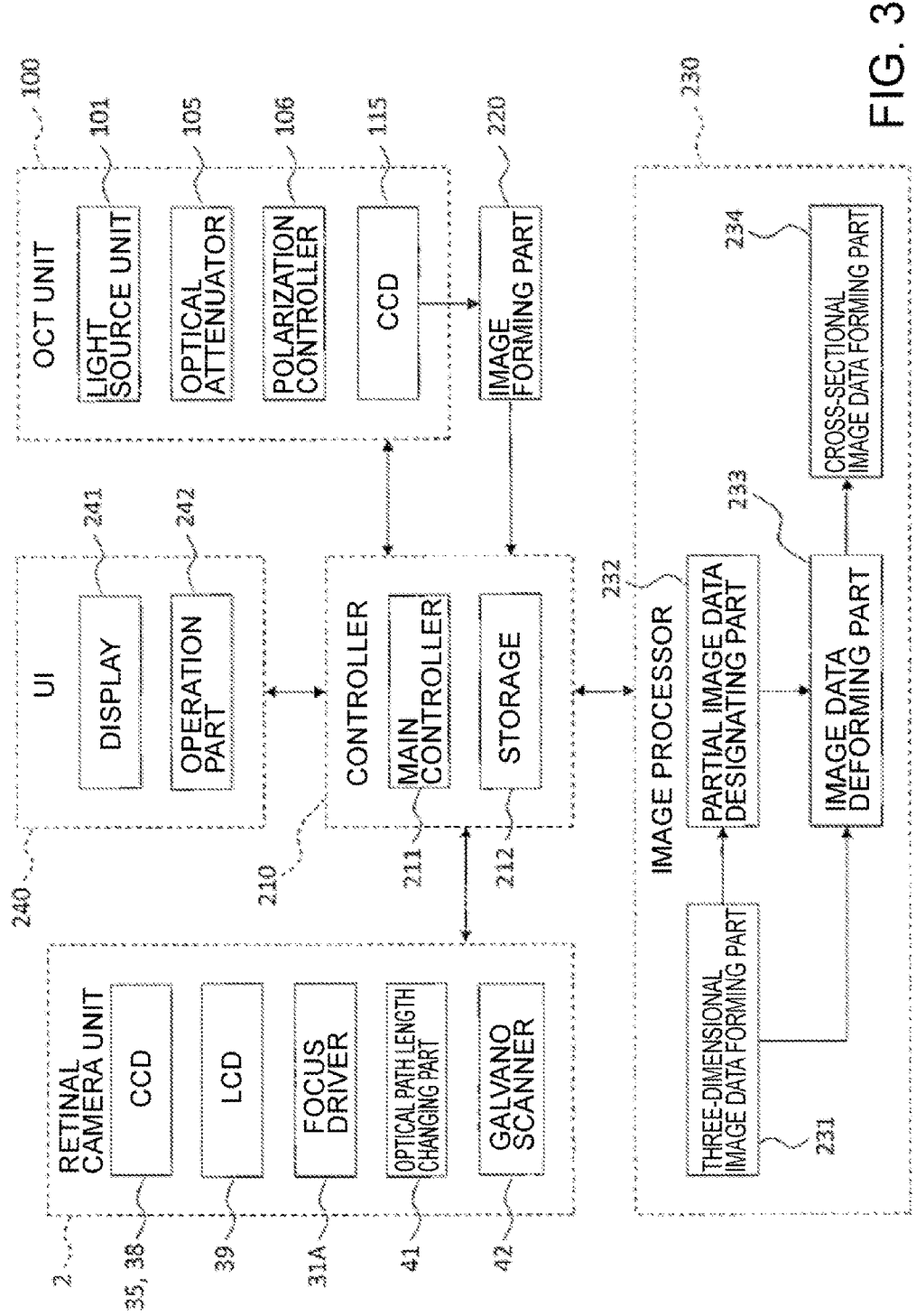
FIG. 3 is a schematic block diagram illustrating a configuration example of an ophthalmologic imaging apparatus according to an embodiment.

The ophthalmologic imaging apparatus according to the present modification includes an image processor 230a illustrated in FIG. 5 instead of the image processor 230 illustrated in FIG. 3. The difference in the configuration of the control system illustrated in FIG. 5 from the configuration of the control system illustrated in FIG. 3 is that a cross section setting part 235a is employed instead of the image data deforming part 233. That is, the image processor 230a includes the three-dimensional image data forming part 231, the partial image data designating part 232, the cross section setting part 235a and the cross-sectional image data forming part 234. The cross section setting part 235a sets a cross section to the three-dimensional image data based on the partial image data. The setting of a cross section by means of the cross section setting part 235a includes at least setting of the orientation of a cross section, and may further include setting of the position of the cross section. When setting the orientation of a cross section, the cross section setting part 235a can set one or more cross sections passing through a site of interest in partial image data (that is, one or more cross sections with the set orientation). When two or more cross sections are set, an interval between cross sections can be set automatically or by hand. It is possible to set a cross section to each of two or more sites of interest. The cross-sectional image data forming part 234 forms cross-sectional image data representing the cross section set by the cross section setting part 235a.

The main controller 211 displays an arbitrary image based on the designated partial image data on the display 241. The user performs an operation for setting a desired cross section based on the displayed image. The displayed image referred to for manual setting of a cross section includes a cross-sectional image or a pseudo three-dimensional image, for example.

A case in which the displayed image is a cross-sectional image is described. The cross-sectional image may be an image representing an arbitrary cross section, and may include one or more transverse cross-sectional images or one or more longitudinal cross-sectional images, for example. The cross-sectional image data forming part 234 applies MPR processing to at least part of partial image data (or at least part of three-dimensional image data including the partial image data). When a cross section to which MPR processing is applied is a transverse cross section and/or a longitudinal cross section, this cross section is set based on three-dimensional coordinate system applied to the partial image data (that is, three-dimensional image data). Note that if the longitudinal cross section is used and the three-dimensional image data is stack data, it is possible to arbitrarily select one or more longitudinal cross-sectional images from among a plurality of longitudinal cross-sectional images included in the stack data. If a cross section to which MPR processing is applied is neither a transverse cross section nor a longitudinal cross section, this cross section is set automatically or manually. In an example of automatic setting, a cross section with a preset orientation can be applied. Alternatively, it is possible to analyze partial image data or three-dimensional image data to specify the site of interest and to set a cross section with a preset orientation so as to pass through the specified site of interest. In an example of manual setting, the image processor 230a applies a predetermined rendering processing (MPR, volume rendering, or the like) to generate image data for display, and the main controller 211 displays an image based on the generated image data on the display 241. The user can refer to the displayed image and set a cross section.

When the displayed image is a pseudo three-dimensional image, the image processor 230a applies volume rendering or the like to at least part of partial image data (or at least part of three-dimensional image data including the partial image data), thereby forming pseudo three-dimensional image data. The main controller 211 displays an image (pseudo three-dimensional image) based on the pseudo three-dimensional image data on the display 241.

Figure 6:
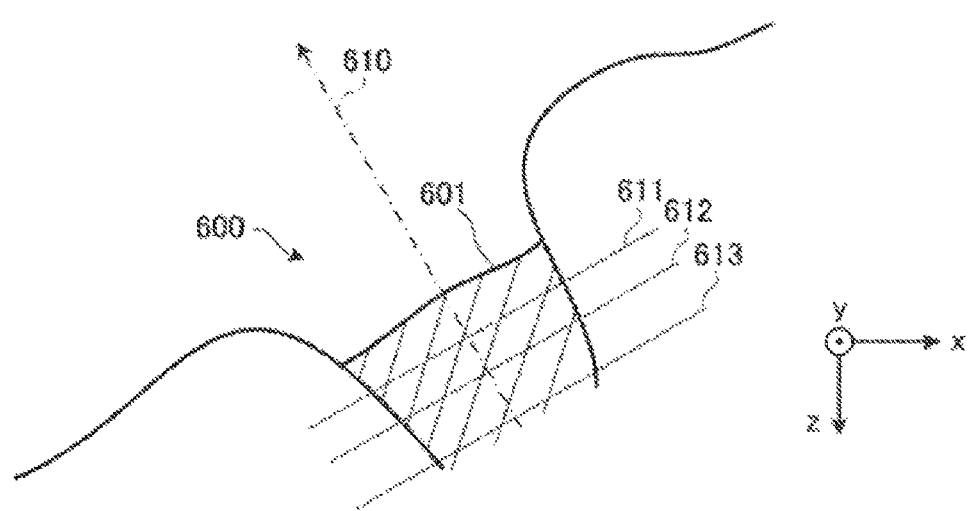
FIG. 6 is a schematic diagram illustrating an operation example of a third modification of an embodiment.

FIG. 6 schematically illustrates a longitudinal cross-sectional image of an optic disc area displayed on the display 241. An optic disc area 600 represents a cribrosa lamina area 601. A plurality of hole parts are represented in the cribrosa lamina area 601. Observation of the cribrosa lamina area 601 is sometimes useful in diagnosis of ophthalmologic diseases (glaucoma, in particular).

The user designates a cross section by designating the orientation of a cross section (the normal direction of a cross section) or designating both the position and orientation of a cross section. For example, when the user designates a normal direction 610 of the upper surface of the cribrosa lamina area 601 by means of the operation part 242, the cross section setting part 235a sets a cross section with the designated direction to the three-dimensional image data. In the case of a longitudinal cross-sectional image or the like, the cross section setting part 235a is capable of finding the orientation of the hole parts and setting a cross section based on the orientation of the hole parts found.

As another example, if the user designates a site of interest in the cribrosa lamina area 601, the cross section setting part 235a is capable of obtaining a cross section based on the site of interest designated. For example, when the upper surface of the cribrosa lamina area 601 is designated as a site of interest, the cross section setting part 235a finds the orientation of the upper surface designated. In this processing, a tangent line at a predetermined position (such as the center position) of the upper surface is calculated, and the orientation of the tangent line is used as the orientation of the upper surface (note that smoothing processing of the upper surface is performed in advance as needed). Alternatively, the orientation of the upper surface can be defined based on a plurality of positions on the upper surface. An example thereof is capable of finding a line segment connecting both ends of the upper surface and defining the direction orthogonal to the line segment as the orientation of the upper surface. Another example is capable of finding directions at a plurality of positions on the upper surface and defining a statistic (the mode, average, or the like) as the orientation of the upper surface.

The cross-sectional image data forming part 234 forms cross-sectional image data representing the cross section set by the cross section setting part 235a. The main controller 211 displays a cross-sectional image based on the cross-sectional image data formed by the cross-sectional image data forming part 234 on the display 241. With such processing, the morphology of an arbitrary cross section can be observed. Further, the orientation and distribution (three-dimensional distribution) of the hole parts can be easily comprehended.

The cross-sectional image data forming part 234 may be configured to form cross-sectional image data representing a cross section orthogonal to the cross section set by the cross section setting part 235a (the cross sections 611 to 613 in FIG. 6, for example). The cross sections 611 to 613 may not be parallel to each other. The image processor 230a is capable of forming a feature enhanced image by adding data of several pixels (7 or 8 pixels, for example) arranged in the cross section direction in a plurality of cross-sectional images formed by the cross-sectional image data forming part 234. Alternatively the image processor 230a is capable of forming a feature enhanced image from three-dimensional image data or partial image data. With such processing, when the cribrosa lamina area 601 is included in partial image data, fiber structures of sites other than hole parts in the cribrosa lamina area 601 can be observed.

When a cross section direction is designated by hand, the main controller 211 is capable of displaying, on the display 241, selection information in which a plurality of cross section directions is selectably presented. An example of the selection information is a drop-down list in which a plurality of cross section directions is listed. The user selects a desired cross section direction from among the plurality of cross section directions presented in the selection information by means of the operation part 242. Alternatively, the main controller 211 displays, on the display 241, a numerical value input screen to which up/down buttons for inputting angles of the x-direction, the y-direction and the z-direction of cross section direction. The user operates the up button/down button by means of the operation part 242, thereby increasing/decreasing the numerical values (angles) displayed on the numerical value input screen with the up/down buttons. The main controller 211 is capable of displaying an icon (arrow) indicating a cross section direction over an image and manually rotating the icon, thereby designating a cross section direction.

(Automatic Designation of Direction of Cross Section of Partial Image Data)

Figure 7:
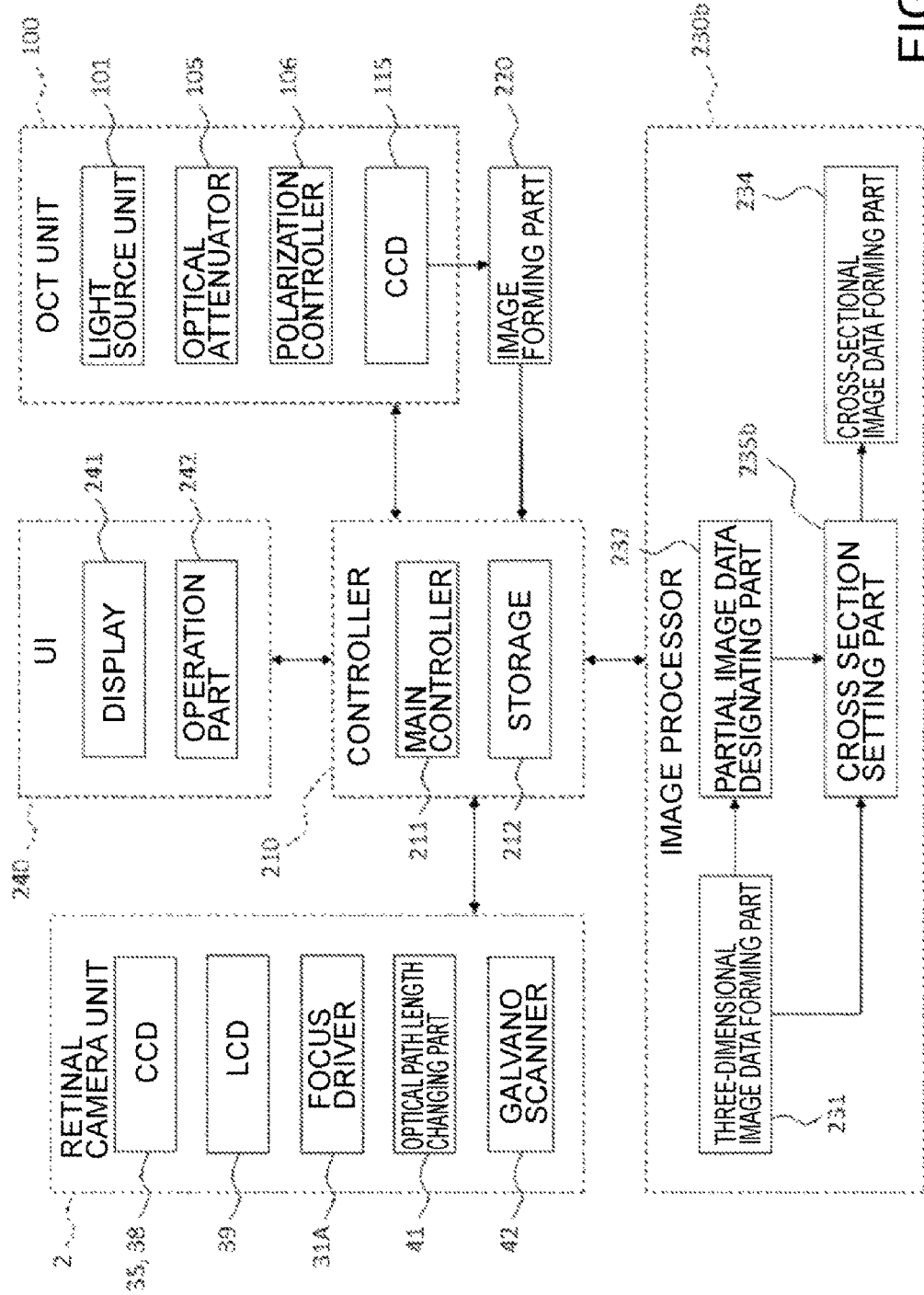
FIG. 7 is a schematic block diagram illustrating a configuration example of a third modification of an embodiment.

FIG. 7 illustrates a configuration of the control system of an ophthalmologic imaging apparatus according to a third modification of the embodiment. FIG. 7 illustrates a configuration example of the control system applicable to a case of automatically designating a direction of a cross section to a partial image data. In FIG. 7, the same numeral symbols are assigned to like parts in FIG. 3, and description thereof are omitted unless required. An arbitrary processing described in the above manual designation can be employed in the present example.

The ophthalmologic imaging apparatus according to the present modification includes an image processor 230b illustrated in FIG. 7 instead of the image processor 230 illustrated in FIG. 3. The difference in the configuration of the control system illustrated in FIG. 7 from the configuration of the control system illustrated in FIG. 3 is that a cross section setting part 235b is employed instead of the image data deforming part 233. That is, the image processor 230b includes the three-dimensional image data forming part 231, the partial image data designating part 232, the cross section setting part 235b and the cross-sectional image data forming part 234. The cross section setting part 235b analyzes partial image data designated by the partial image data designating part 232 to find a cross section direction, and sets the found cross section to the partial image data. The cross-sectional image data forming part 234 forms cross-sectional image data representing the cross section set by the cross section setting part 235b.

The cross section setting part 235b is capable of determining a cross section of the partial image data based on a longitudinal cross-sectional image of the partial image data, and setting the determined cross section to the partial image data.

For example, it is assumed that the cribrosa lamina area 601 is included in the partial image data. The cross section setting part 235b analyzes the partial image data to specify the upper surface of the cribrosa lamina area 601, and determines the position and/or orientation of a cross section based on an inclination angle of the specified upper surface. The cross section setting part 235b sets the determined cross section to the three-dimensional image data.

Alternatively, the cross section setting part 235b extracts parts with brightness equal to or smaller than a preset threshold as hole parts of the cribrosa lamina area 601 from brightness information of pixels near the cribrosa lamina area 601, and creates a wire-frame model representing areas of the extracted hole parts. The cross section setting part 235b determines, as the orientation of a cross section (orientation of the hole parts), the direction of positional shift between a start point and an end point in the wire-frame model, a tangent direction at a predetermined position in the wire-frame model, or an incline direction of the line segment connecting predetermined two positions in the wire-frame model, and sets the determined cross section to the partial image data.

The cross section setting part 235b is capable of determining a cross section of the partial image data based on a transverse cross-sectional image of the partial image data, and setting the determined cross section to the partial image data.

In this case, the cross section setting part 235b specifies the state of connectedness of hole parts in the cribrosa lamina area 601 in a plurality of transverse cross sections that are parallel to each other, determines the orientation of a cross section (orientation of the hole parts) from the specified state of connectedness, and sets the determined cross section to the partial image data. Note that the cross section setting part 235b specifies the state of connectedness of hole parts in the cribrosa lamina area 601 in a plurality of transverse cross sections that are not parallel to each other.

The cross-sectional image data forming part 234 forms cross-sectional image data representing the cross section set by the cross section setting part 235b. The main controller 211 displays a cross-sectional image based on the cross-sectional image data formed by the cross-sectional image data forming part 234 on the display 241. With such processing, the morphology of an arbitrary cross section can be observed. Further, the orientation and distribution (three-dimensional distribution) of the hole parts can be easily comprehended.

The cross-sectional image data forming part 234 may be configured to form cross-sectional image data representing a cross section orthogonal to the cross section set by the cross section setting part 235b. The cross sections 611 to 613 may not be parallel to each other. The image processor 230b is capable of forming a feature enhanced image by adding data of several pixels (7 or 8 pixels, for example) arranged in the cross section direction in a plurality of cross-sectional images formed by the cross-sectional image data forming part 234. Alternatively the image processor 230b is capable of forming a feature enhanced image from three-dimensional image data or partial image data. With such processing, when the cribrosa lamina area 601 is included in partial image data, fiber structures of sites other than hole parts in the cribrosa lamina area 601 can be observed.

The cross section setting part 235b can set a cross section based on the vicinity of the cribrosa lamina area 601 in partial image data. In this case, the cross section setting part 235b specifies the orientation of the bottom face of the optic disc in the vicinity of the cribrosa lamina area 601, and determines the orientation of a cross section in the cribrosa lamina area 601 based on the specified orientation of the bottom face of the optic disc.

As described above, since the third modification forms cross-sectional image data representing a cross section of an arbitrary direction for partial image data designated from three-dimensional image data, the morphology of an arbitrary cross section can be observed. For example, when partial image data includes a cribrosa lamina area, fiber structures of sites other than hole parts in the cribrosa lamina area 601 can be observed. Note that objects of the above processing are not so limited and the above processing can be applied to an arbitrary site.

<Ophthalmologic Image Display Apparatus>

Ophthalmologic image display apparatuses according to embodiments are described. Detailed descriptions are omitted for matters, among the matters described below, substantially the same as the ophthalmologic imaging apparatus 1 described above.

Figure 8:
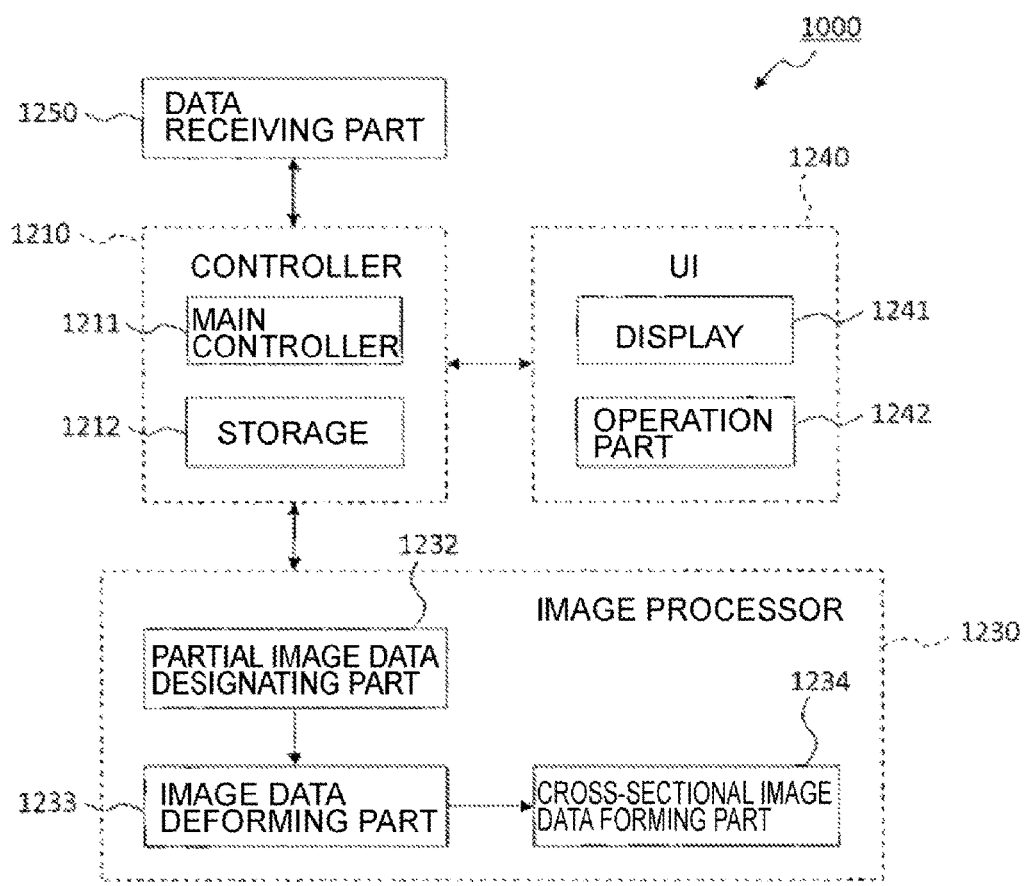
FIG. 8 is a schematic block diagram illustrating a configuration example of an ophthalmologic image display apparatus according to an embodiment.

An ophthalmologic image display apparatus 1000 illustrated in FIG. 8 receives three-dimensional image data of an eye acquired by an external OCT apparatus, deforming the three-dimensional image data, and displays a cross-sectional image based on the deformed three-dimensional image data.

The ophthalmologic image display apparatus 1000 includes a controller 1210, an image processor 1230, a user interface 1240, and a data receiving part 1250.

The data receiving part 1250 receives three-dimensional image data of an eye acquired by an external OCT apparatus. Further, the data receiving part 1250 receives front image data of the eye acquired by an external ophthalmologic imaging apparatus. The data receiving part 1250 includes a configuration according to an aspect of reception of data such as communication interface, a drive device, and the like. The data receiving part 1250 functions as a "receiving part".

The controller 1210 performs control of each part of the ophthalmologic image display apparatus 1000 and various kinds of arithmetic processing. The controller 1210 includes a microprocessor, a RAM, a ROM, a hard disk drive, a communication interface, and the like. The controller 1210 includes a main controller 1211 and storage 1212.

The main controller 1211 performs various kinds of control and various kinds of arithmetic processing. The main controller 1211 functions as the "display controller". The storage 1212 stores various kinds of data. The storage 1212 stores, for example, OCT image data (such as three-dimensional image data and the like), front image data, eye information, and the like. Further, the storage 1212 stores various kinds of programs and data for operating the ophthalmologic image display apparatus 1000.

The image processor 1230 performs various kinds of image processing and analysis. The image processor 1230 includes a partial image data designating part 1232, an image data deforming part 1233 and a cross-sectional image data forming part 1234. The partial image data designating part 1232 functions as the "designating part". The image data deforming part 1233 functions as the "deforming part". The cross-sectional image data forming part 1234 functions as the "forming part".

The partial image data designating part 1232 performs the same processing as the partial image data designating part 232 of the ophthalmologic imaging apparatus 1, thereby designating partial image data that is a part of the three-dimensional image data corresponding to a specific site of the eye E.

The image data deforming part 1233 performs the same processing as the image data deforming part 233 of the ophthalmologic imaging apparatus 1, thereby deforming the three-dimensional image data such that the partial image data designated by the partial image data designating part 1232 is deformed into a predetermined shape.

The cross-sectional image data forming part 1234 performs the same processing as the cross-sectional image data forming part 234 of the ophthalmologic imaging apparatus 1, thereby forming cross-sectional image data based on the three-dimensional image data deformed by the image data deforming part 1233 (deformed three-dimensional image data).

The image processor 1230 that functions as above includes, for example, a microprocessor, a RAM, a ROM, a hard disk drive, a circuit board, and the like. Computer programs causing the microprocessor to realize the above functions are stored in storage devices such as the hard disk drive in advance.

The user interface 1240 includes a display 1241 and an operation part 1242. The display 1241 includes an arbitrary display device. The operation part 1242 includes an arbitrary operation device.

The ophthalmologic image display apparatus 1000 displays a screen like the window 300 described above, for example. Using such a screen, like operations as with the ophthalmologic imaging apparatus 1 can be performed.

According to the ophthalmologic image display apparatus 1000 thus configured, a cross-sectional image can be displayed in which the specific site of the eye is represented in the predetermined shape. Accordingly, while paying attention to the specific site during observation, relations between the specific site and other sites can be easily comprehended. Therefore, a new technique of ophthalmologic diagnostic imaging can be realized.

Any matter regarding the ophthalmologic imaging apparatus 1 in the above embodiments and modifications can be applied to the ophthalmologic image display apparatus 1000.

In the above embodiments and modifications, the image data deforming part 233 is not limited to a configuration that deforms three-dimensional image data such that partial image data is deformed into a predetermined shape to create new three-dimensional image data.

The ophthalmologic image display apparatus 1000 may include a receiving part, a designating part, a cross section setting part, a forming part, and a display controller. The receiving part receives three-dimensional image data of an eye acquired by using optical coherence tomography. The designating part is used for designating partial image data that is a part of the three-dimensional image data corresponding to a specific site of the eye. The cross section setting part sets a cross section of the three-dimensional image data based on the partial image data. The forming part forms cross-sectional image data representing the cross section set by the cross section setting part. The display controller displays an image based on the cross-sectional image data on a display means.

Computer programs for implementing the above embodiments may be stored in any kinds of computer-readable recording media. Examples of such recording media include an optical disk, semiconductor memory, magneto-optic disk (CD-ROM, DVD-RAM, DVD-ROM, MO, etc.), magnetic storage (a hard disk, a Floppy Disk™, ZIP, etc.), etc.

The programs may be transmitted through networks such as internet, LAN, etc.

The configurations described above are merely examples for implementing the present invention. It is possible to make arbitrary modifications (omission, replacement, addition, etc.) within the scope of the present invention.

What is claimed is:

1. An ophthalmologic imaging apparatus comprising:
    an acquiring part configured to acquire three-dimensional image data of an eye by using optical coherence tomography;
    a designating part configured to process designated partial image data by expanding an image area designated by a user that is a cross-sectional image part of the three-dimensional image data corresponding to a specific site of the eye to a data area corresponding to totality of the three dimensional image data of the specific site, based on pixel values of the three dimensional image data;
    a deforming part configured to deform the three-dimensional image data such that a partial image corresponding to the processed designated partial image data is deformed into a predetermined shape to create new three-dimensional image data by shifting sequences of voxels on A-lines in a direction of light irradiated to the eye in optical coherence tomography such that positions of the voxels corresponding to the partial image data are arranged in the predetermined shape;
    a forming part configured to form cross-sectional image data based on the new three-dimensional image data; and
    a display controller configured to display an image based on the cross-sectional image data on a display means.

2. The ophthalmologic imaging apparatus of claim 1, wherein
    the partial image is a two-dimensional area in the three-dimensional image data, and
    the deforming part deforms the three-dimensional image data such that the two-dimensional area is deformed into a planar shape or a predetermined curved shape.

3. The ophthalmologic imaging apparatus of claim 2, wherein
    the forming part forms, as the cross-sectional image data, transverse cross-sectional image data in a transverse section that is substantially orthogonal to a traveling direction of light irradiated to the eye in optical coherence tomography, and
    the display controller displays a transverse cross-sectional image based on the transverse cross-sectional image data on the display means.

4. The ophthalmologic imaging apparatus of claim 3, further comprising a first operation part configured for designating a position of the transverse section, wherein
    the forming part forms new transverse cross-sectional image data in a transverse section designated using the first operation part, and
    the display controller updates a transverse cross-sectional image displayed on the display means based on the new transverse cross-sectional image data.

5. The ophthalmologic imaging apparatus of claim 3, wherein
    the forming part further forms, as the cross-sectional image data, longitudinal cross-sectional image data in a longitudinal section orthogonal to the transverse section, and
    the display controller arranges and displays a longitudinal cross-sectional image based on the longitudinal cross-sectional image data and the transverse cross-sectional image, displays a longitudinal section position image indicating a sectional position of the longitudinal cross-sectional image together with the transverse cross-sectional image, and displays a transverse section position image indicating a sectional position of the transverse cross-sectional image together with the longitudinal cross-sectional image.

6. The ophthalmologic imaging apparatus of claim 5, wherein
    the forming part forms, as the longitudinal cross-sectional image data, first longitudinal cross-sectional image data and second longitudinal cross-sectional image data in two longitudinal sections orthogonal to each other, and
    the display controller arranges and displays a first longitudinal cross-sectional image based on the first longitudinal cross-sectional image data, a second longitudinal cross-sectional image based on the second longitudinal cross-sectional image data and the transverse cross-sectional image, displays a first longitudinal section position image indicating a sectional position of the first longitudinal cross-sectional image and a second longitudinal section position image indicating a sectional position of the second longitudinal cross-sectional image together with the transverse cross-sectional image, and displays the transverse section position image indicating a sectional position of the transverse cross-sectional image together with each of the first and second longitudinal cross-sectional images.

7. The ophthalmologic imaging apparatus of claim 5, further comprising a second operation part configured for designating a position of the longitudinal section, wherein
    the forming part forms new longitudinal cross-sectional image data in a longitudinal section designated using the second operation part, and
    the display controller updates a longitudinal cross-sectional image displayed on the display means based on the new longitudinal cross-sectional image data, and changes a display position of the longitudinal section position image with respect to the transverse cross-sectional image based on the designated longitudinal section.

8. The ophthalmologic imaging apparatus of claim 5, further comprising a photographing part configured to photograph the eye to obtain front image data, wherein
    the display controller arranges and displays a front image based on the front image data, the transverse cross-sectional image and the longitudinal cross-sectional image, and displays the longitudinal section position image together with the front image.

9. The ophthalmologic imaging apparatus of claim 3, further comprising a photographing part configured to photograph the eye to obtain front image data, wherein
    the display controller displays a front image based on the front image data and the transverse cross-sectional image overlapped with each other.

10. The ophthalmologic imaging apparatus of claim 3, further comprising
    a photographing part configured to photograph the eye to obtain front image data, and
    an analyzer configured to analyze the new three-dimensional image data to obtain distribution information that represents distribution of distances between a first tissue and a second tissue of the eye, wherein the display controller displays a front image based on the front image data and a distribution image based on the distribution information overlapped with each other.

11. The ophthalmologic imaging apparatus of claim 1, further comprising a third operation part, wherein the forming part forms standard cross-sectional image data in a standard section substantially along a traveling direction of light irradiated to the eye in optical coherence tomography based on the three-dimensional image data acquired by the acquiring part, the display controller displays a standard cross-sectional image based on the standard cross-sectional image data on the display means, and when an image area in the standard cross-sectional image is designated using the third operation part, the designating part analyzes the three-dimensional image data based on the designated image area to perform designation of the partial image data.

12. The ophthalmologic imaging apparatus of claim 1, further comprising a fourth operation part, wherein the display controller displays selection information in which a plurality of tissues of an eye is selectably presented on the display means, and when a tissue of the plurality of tissues presented in the selection information is selected using the fourth operation part, the designating part performs designation of the partial image data by analyzing the three-dimensional image data based on the selected tissue to specify a part of the three-dimensional image data corresponding to the selected tissue.

13. The ophthalmologic imaging apparatus of claim 12, wherein the forming part forms standard cross-sectional image data in a standard section substantially along a traveling direction of light irradiated to the eye in optical coherence tomography based on the three-dimensional image data acquired by the acquiring part, and the display controller displays a standard cross-sectional image based on the standard cross-sectional image data on the display means, and when a tissue of the plurality of tissues is selected using the fourth operation part, the display controller changes a display aspect of a part of the standard cross-sectional image corresponding to the selected tissue.

14. The ophthalmologic imaging apparatus of claim 1, wherein the deforming part is configured to deform the partial image corresponding to the entire processed designated partial image data is deformed into the predetermine shape, and wherein the predetermined shape comprises one of planar shape and a curved shape.

15. The ophthalmologic imaging apparatus of claim 14, wherein the deforming part is configured to deform the partial image into a curved shape comprising one of a curved shape according to a default setting, a shape preset according to examination contents, a shape preset according to kinds of specific tissue site and a shapes arbitrarily set by a user.

16. An ophthalmologic image display apparatus comprising:

a receiving part configured to receive three-dimensional image data of an eye acquired by using optical coherence tomography;

a designating part configured to process designated partial image data by expanding an image area designated by a user that is a cross-sectional image part of the three-dimensional image data corresponding to a specific site of the eye to a data area corresponding to totality of the three dimensional image data of the specific site, based on pixel values of the three dimensional image data;

a deforming part configured to deform the three-dimensional image data such that a partial image corresponding to the processed designated partial image data is deformed into a predetermined shape to create new three-dimensional image data by shifting sequences of voxels on A-lines in a direction of light irradiated to the eye in optical coherence tomography such that positions of the voxels corresponding to the partial image data are arranged in the predetermined shape;

a forming part configured to form cross-sectional image data based on the new three-dimensional image data; and a display controller configured to display an image based on the cross-sectional image data on a display means.

17. The ophthalmologic image display apparatus of claim 16, wherein the deforming part is configured to deform the partial image corresponding to the entire processed designated partial image data is deformed into the predetermine shape, and wherein the predetermined shape comprises one of planar shape and a curved shape.

18. The ophthalmologic image display apparatus of claim 17, wherein the deforming part is configured to deform the partial image into a curved shape comprising one of a curved shape according to a default setting, a shape preset according to examination contents, a shape preset according to kinds of specific tissue site and a shapes arbitrarily set by a user.

* * * * *